United States Patent
Markel et al.

(10) Patent No.: US 6,544,260 B1
(45) Date of Patent: *Apr. 8, 2003

(54) METHOD FOR TREATING TISSUE IN ARTHROSCOPIC ENVIRONMENT USING PRECOOLING AND APPARATUS FOR SAME

(75) Inventors: Mark Markel, Madison, WI (US); Hugh R. Sharkey, Woodside, CA (US); Gary S. Fanton, Portola Valley, CA (US)

(73) Assignee: Oratec Interventions, Inc., Menlo Park, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/476,018

(22) Filed: Dec. 31, 1999

Related U.S. Application Data

(63) Continuation-in-part of application No. 08/700,196, filed on Aug. 20, 1996, now Pat. No. 6,068,628.

(51) Int. Cl.[7] ............................................. A61B 18/18
(52) U.S. Cl. ............................ 606/41; 606/45; 606/49; 606/50; 607/102
(58) Field of Search .............................. 606/41, 42, 45, 606/46, 48, 49–50, 34, 37–40, 31–33; 607/100–103, 105, 109, 113, 116

(56) References Cited

U.S. PATENT DOCUMENTS

| | | |
|---|---|---|
| 164,184 A | 8/1875 | Kidder |
| 300,155 A | 6/1884 | Starr |
| 371,664 A | 10/1887 | Brannan et al. |
| 452,220 A | 5/1891 | Gunning |
| 1,314,855 A | 9/1919 | Carpenter |
| 1,366,756 A | 1/1921 | Wappler |
| 1,731,627 A | 10/1929 | Johnson et al. |
| 1,735,271 A | 12/1929 | Groff |
| 1,814,791 A | 7/1931 | Ende |
| 1,908,583 A | 5/1933 | Wappler |
| 1,916,722 A | 7/1933 | Ende |
| 1,932,258 A | 10/1933 | Wappler |
| 1,943,543 A | 1/1934 | McFadden |
| 1,983,669 A | 11/1934 | Kimble |
| 2,002,594 A | 5/1935 | Wappler et al. |
| 2,004,559 A | 6/1935 | Wappler et al. |
| 2,050,904 A | 8/1936 | Trice |

(List continued on next page.)

FOREIGN PATENT DOCUMENTS

GB  2160102 A  12/1985

OTHER PUBLICATIONS

Lee Beadling, *Bi–Polar electrosurgical devices: Sculpting the future of arthroscopy*, Orthopedics Today, Jan. 1997, vol. 17, No. 1, Slack, Inc., Medical Publisher.

*Primary Examiner*—Roy D. Gibson
(74) *Attorney, Agent, or Firm*—Fish & Richardson P.C.

(57) ABSTRACT

A thermal energy delivery apparatus has a probe including a distal end and a proximal end. A first electrode is positioned at the distal end of the probe. The first electrode is configured to deliver sufficient thermal energy to a fibrillated cartilage surface to reduce a level of fibrillation of the fibrillated cartilage surface. A cabling is coupled to the proximal end of the probe. A method for thermal protection of non-targeted tissues that may be exposed to thermal probes used during arthroscopic procedures includes a pre-procedural cooling Lavage. The pre-cooled tissues provide a convective buffer for tissues not intended for thermal intervention, thereby reducing collateral damage.

38 Claims, 9 Drawing Sheets

(2 of 9 Drawing Sheet(s) Filed in Color)

U.S. PATENT DOCUMENTS

| | | | |
|---|---|---|---|
| 2,056,377 A | 10/1936 | Wappler | |
| 2,224,464 A | 12/1940 | Wolf | |
| 2,275,167 A | 3/1942 | Bierman | |
| 2,888,928 A | 6/1959 | Seiger | |
| 3,152,590 A | 10/1964 | Zurdo et al. | |
| 3,163,165 A | 12/1964 | Isakawa | |
| 3,460,539 A | 8/1969 | Anhalt, Sr. | |
| 3,595,239 A | 7/1971 | Perersen | |
| 3,768,482 A | 10/1973 | Shaw | |
| 3,821,510 A * | 6/1974 | Muncheryan | |
| 3,828,780 A | 8/1974 | Morrison, Jr. | |
| 3,870,047 A | 3/1975 | Gonser | |
| 3,901,242 A | 8/1975 | Storz | |
| 3,902,494 A | 9/1975 | Haberlin | |
| 3,920,021 A | 11/1975 | Hiltebrandt | |
| 3,920,022 A | 11/1975 | Pastor | |
| 3,938,527 A | 2/1976 | Rioux et al. | |
| 3,987,795 A | 10/1976 | Morrison | |
| 4,927,420 A | 5/1990 | Newkirk et al. | |
| 5,027,792 A * | 7/1991 | Meyer | |
| 5,277,696 A | 1/1994 | Hagen | |
| 5,281,218 A | 1/1994 | Imran | |
| 5,409,481 A | 4/1995 | Poppas et al. | |
| 5,428,699 A * | 6/1995 | Pon | 385/31 |
| 5,431,649 A * | 7/1995 | Mulier et al. | 606/41 |
| 5,437,662 A * | 8/1995 | Nardella | 606/40 |
| 5,458,596 A * | 10/1995 | Lax et al. | 606/31 |
| 5,486,170 A | 1/1996 | Winston et al. | |
| 5,514,130 A | 5/1996 | Baker | |
| 5,643,255 A | 7/1997 | Organ | |
| 5,697,882 A * | 12/1997 | Eggers et al. | 604/114 |
| 5,786,705 A | 7/1998 | Baker | |
| 5,814,040 A | 9/1998 | Nelson et al. | |
| 6,135,999 A | 10/2000 | Fanton et al. | |

* cited by examiner

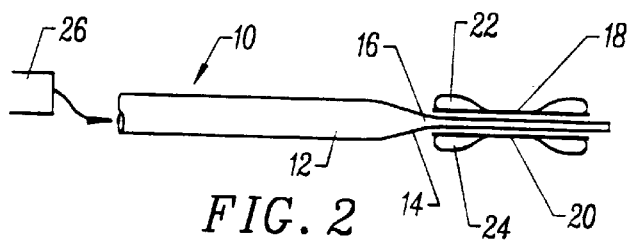
FIG. 2
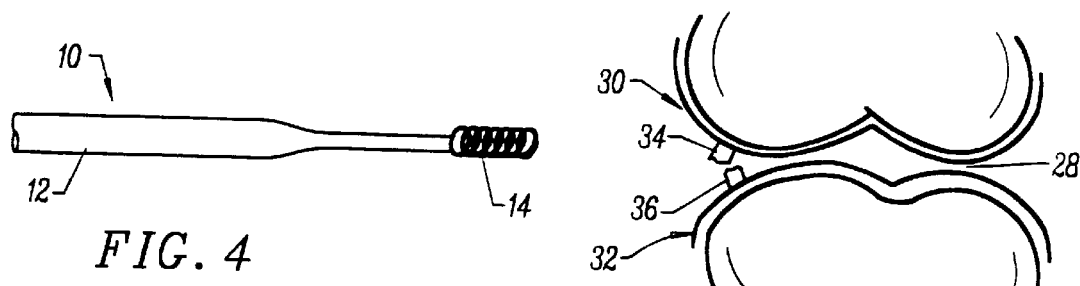
FIG. 4
FIG. 3
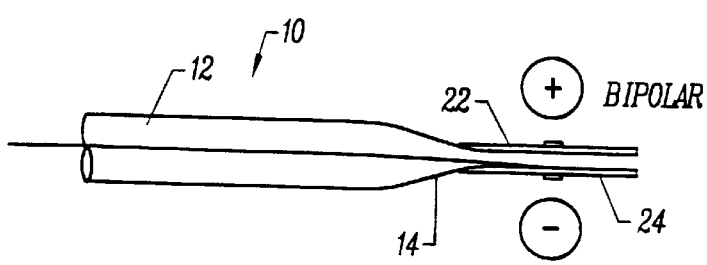
FIG. 5
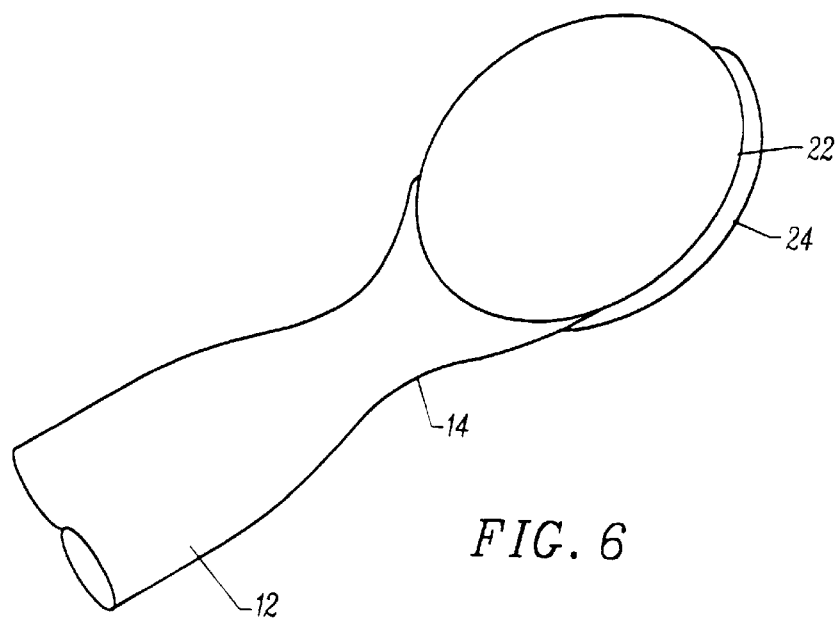
FIG. 6

In vitro work with TAC-S Probe
Lavage temperature, power settings and probe temperature are labeled

METHOD FOR TREATING TISSUE IN ARTHROSCOPIC ENVIRONMENT USING PRECOOLING AND APPARATUS FOR SAME

CROSS-REFERENCE TO RELATED APPLICATION

This application is a continuation-in-part under 35 U.S.C. §120 of copending U.S. Ser. No. 08/700,196, filed Aug. 20, 1996, now the U.S. Pat. No. 6,068,628 entire contents of which are hereby incorporated herein by reference as if fully set forth herein.

BACKGROUND OF THE INVENTION

1. Field of the Invention

This invention relates generally to a method and apparatus for treating chondromalacia, and more particularly to a method and apparatus that treats chondromalacia with minimal disruption of the cartilage bed of the knee.

This invention also relates generally to thermal therapy techniques for treating joint pathologies arthroscopically. More specifically, techniques to manipulate the thermal dynamic aspects of the joint capsule environment as approached arthroscopically.

2. Description of Related Art

The normal function of joints in humans depends on the distribution of relatively large forces across the body surfaces. In diarthrodial joints the magnitude of the joint forces reaches levels four to seven times body weight. These forces applied to joints are dispersed by articular cartilage. Cartilage function occurs via a highly organized extracellular matrix maintaining a fixed charge density and possessing a high affinity for water.

Normal articular cartilage consists of an assembly of large and small proteoglycans, collagens, hyaluronic acid and glycoproteins. These matrix macromolecules originate from chondrocytes localized in a nonrandom pattern through the cartilage matrix. In normal joints, chondrocytes do not proliferate; dividing chondrocytes indicate-a change in cartilage homeostasis, either as regeneration or attempted repair.

Chondromalacia occurs when cartilage beds in joints become worn and strands of cartilage distended away from their respective cartilage beds and extend into the joint capsule. The cartilage surface becomes visibly disrupted, fissured and fibrillated. This has deterious effects on the mechanical properties of articular cartilage. This distension has been associated with knee pain. Treatment to date has included surgical intervention. In one arthroscopic procedure, a shaver is introduced through an arthroscope and is used to remove the strands of disrupted and fibrillated cartilage. However, this treatment can disrupt and remove part of the normal cartilage bed and does not restore a smooth surface nor the mechanical function.

It would be desirable to provide a method and apparatus treating fibrillated cartilage joint surfaces or irregular cartilage joint surfaces by delivering sufficient thermal energy to reduce a level of fibrillation or irregularity of the fibrillated cartilage joint surface or the irregular cartilage joint surface. It would also be desirable to modify the fibrillated cartilage surface to a smooth surface. It would be further desirable to treat chondromalacia by reducing a level of fibrillation or irregularity of a fibrillated or irregular cartilage joint surface.

Arthroscopic interventions include a variety of modalities in the treatment of various joint pathologies. These modalities include mechanical shavers, electrosurgical devices, mechanical burrs and drills and electrothermal interventions for the modification of collagenous structures. Heat may be generated by mechanical means as a byproduct of friction, or by ohmic (resistive) heating as a result of electromagnetic currents passing through tissues generating heat. In certain instances, thermal insult of the adjacent structures can have significant implications and must be minimized to the maximum extent possible. The inadvertent exposure to these adjacent tissues can result in the loss of important viable cells not intended for destruction, such as articular cartilage, subchondral bone and neurovascular structures that may reside in close proximity to structures intended for these therapies. One such instance is in the treatment of chondromalacia by electrothermal coagulation of the fibrillated cartilage surface.

Chondromalacia is a condition of the articular cartilage, particularly the knee that is addressed using thermal techniques. Conventional treatment for chondromalacia involves debridement by mechanically cutting or shaving of any non-viable or troublesome tissues at the time of arthroscopic surgery. This condition has also been approached with lasers and conventional electrosurgery devices.

One apparatus and method as described in parent application U.S. Ser. No. 08/700,196, filed Aug. 20, 1996, now pending, describes treating the fibrillated cartilage surflces by utilizing the properties of the collage component of the articular cartilage. These properties allow the doctor to treat chondromalacia or other chondral defects with thermal energy at levels that coagulate the fibrillated or non-intact cartilage tissue, sealing the articular cartilage structures thereof, thereby inhibiting further degradation of the cartilage matrix. The mechanical aspects of the knee joint are thus maintained with little change in articular function.

Thermal chondroplasty utilizing a temperature feedback system has several advantages over the mechanical shaving method. With debridement and mechanical shaving, inadvertent disruption of healthy viable articular cartilage is practically unavoidable and further results in dysfunction of the joint. Further, the resultant surface architecture of the haline cartilage remains discarded whereby remaining articular cartilage strands are still present in the joint area and bits of fibrillated cartilage continue to serve as a source of joint inflammation and pain.

The thermal treatment approach provides both a smooth gliding surface for the corresponding arcticular surfaces and coagulates and seals the fibrillated strands. The fibrillated strands would otherwise break off as a result of further degeneration and mechanical wear due to the pressure of weight bearing and movement during joint articulation. These remnants of cartilage irritate the joint, in particular the synovial lining, which became inflamed from contact with these free floating pieces of tissue and the chemical components that are a byproduct of the breakdown of these tissues.

Concerns related to the use of thermal energy in close proximity to healthy and viable tissues (i.e., non-targeted tissues) include the potential for thermal collateral damage or injury to tissues not intended for removal or treatment. The thermal effect on non-targeted tissues is compounded by the articular cartilage natural characteristic of not having the ability to repair itself or regenerate as with other types of tissue. Thus, temperature feedback control devices and methods limit, but do not all together eliminate these potential adverse effects.

For these reasons, it would be desirable to provide an approach to reducing this type of collateral damage and further limit and reduce the potential for extraneous and collateral thermal exposure of non-targeted tissue. Such an approach should be able to treat targeted cartilage surfaces and other structures found in the arthroscopic setting in conjunction with thermal therapy procedures, and to simultaneously protect healthy and viable non-targeted tissues that are in close proximity to, or are continuous with, tissues targeted for thermal treatment. Such an approach should allow, for example, the treatment of damaged articular cartilage with minimal or no injury to the underlying viable cartilage and subchondral bone or other structures in the diarthrodial joint.

SUMMARY OF THE INVENTION

Accordingly, an object of the invention is to provide a method and apparatus for treating fibrillated or irregular cartilage joint surfaces.

Another object of the invention is to provide a method and apparatus for delivering sufficient thermal energy to reduce a level of fibrillation of a fibrillated cartilage joint surface.

Yet another object of the invention is to provide a method and apparatus for delivering sufficient thermal energy to modify a fibrillated cartilage joint surface to a smooth surface.

A further object of the invention is to provide a method and apparatus for delivering sufficient thermal energy to modify an irregular cartilage joint surface to a smoother surface.

Still a further object of the invention is to provide a method and apparatus for delivering sufficient thermal energy to at least a portion of a plurality of cartilage strands coupled to a fibrillated cartilage surface, and melt the strands onto the fibrillated cartilage surface.

Another object of the invention is to provide a method and apparatus that uses thermal energy to treat chondromalacia.

These and other objects of the invention are achieved in a thermal energy delivery apparatus that has a probe means including a distal end and a proximal end. A first electrode means is positioned at the distal end of the probe means. The first electrode means is configured to deliver sufficient thermal energy to a fibrillated cartilage surface to reduce a level of fibrillation of the fibrillated cartilage surface. A cabling means is coupled to the proximal end of the probe means.

In one embodiment of the invention, an apparatus is configured to be positioned adjacent to a fibrillated cartilage joint surface. A probe means has a distal end and a proximal end. An insulator means has a first surface and a second surface. A first electrode means is positioned on the first surface of the insulator. The first electrode means has a first thermal energy delivery surface configured to deliver sufficient thermal energy to a plurality of cartilage strands coupled to the fibrillated cartilage joint surface to reduce a level of fibrillation of surface. A second electrode means is positioned on the second surface of the insulator. A cable means is coupled to the proximal end of the probe means.

In another embodiment, a method modifies a geometry of a fibrillated cartilage surface. A thermal energy delivery device is provided and includes a probe means with a distal end and a thermal energy delivery surface. A thermal energy source is also provided and coupled to the thermal energy delivery surface. The thermal energy delivery surface is positioned adjacent to the fibrillated cartilage surface in a non-contacting position. Sufficient thermal energy is delivered from the thermal energy delivery surface to reduce a level of fibrillation of the fibrillated cartilage surface.

The method and apparatus of the present invention can also be used to decrease the level of irregularity of an irregular cartilage surface.

The apparatus of the present invention may also include a sensor means positioned at the distal end of the probe means. A comparator means is provided and compares a measured temperature value at the sensor means with a predetermined temperature value. The comparator means generates a disabling signal if the measured temperature value exceeds the predetermined maximum temperature value. A communication means is provided and communicates the disabling signal to the thermal energy source means to cease further delivery of energy from the thermal energy source means to the first electrode means.

In various embodiments of the invention, sufficient thermal energy is delivered from the thermal energy delivery surface to modify the fibrillated cartilage surface to a smooth surface. Thermal energy is delivered from the thermal energy delivery surface to create a less fibrillated, fibrillated cartilage surface. Thermal energy is delivered from the thermal energy delivery surface to cause at least a portion of a plurality of cartilage strands coupled to the fibrillated cartilage surface to create a smoothened cartilage surface. Thermal energy is delivered from the thermal energy delivery surface to cause at least a portion of a plurality of cartilage strands coupled to the fibrillated cartilage surface to melt onto the fibrillated cartilage surface. At least a portion of a plurality of cartilage strands are melted to create a smoothened cartilage surface.

A method according the invention includes the precooling of tissue by means of an irrigating solution cooled to a very low temperature. The cooled solution is used to Lavage the joint for a period of time prior to the application of thermal therapeutic energy. It will be appreciated that such low temperatures decrease the temperature of the associated structures exposed within the field of the synovial cavity, thus providing a conventive thermal offset that will limit any temperature rise in response to any thermal energy applied to the tissue. The presence of the lower offset temperature protects the non-targeted tissue from collateral damage as a result of the thermal treatment.

A further understanding of the nature and advantages of the present invention will become apparent by reference to the following specification and drawings.

BRIEF DESCRIPTION OF THE FIGURES

The patent or application file contains at least one drawing executed in color. Copies of this patent or patent application publication with color drawing(s) will be provided by the Office upon request and payment of the necessary fee.

A clear conception of the advantages and features constituting the invention, and of the components and operation of model systems provided with the invention, will become more readily apparent by referring to the exemplary, and therefore nonlimiting, embodiments illustrated in the drawings accompanying and forming a part of this specification, wherein like reference characters (if they occur in more than one view) designate the same parts. It should be noted that the features illustrated in the drawings are not necessarily drawn to scale.

The file of this patent contains at least one drawing executed in color. Copies of this patent with color drawings will be provided by the U.S. Patent and Trademark Office upon request and payment of the necessary fee.

Figure 1:
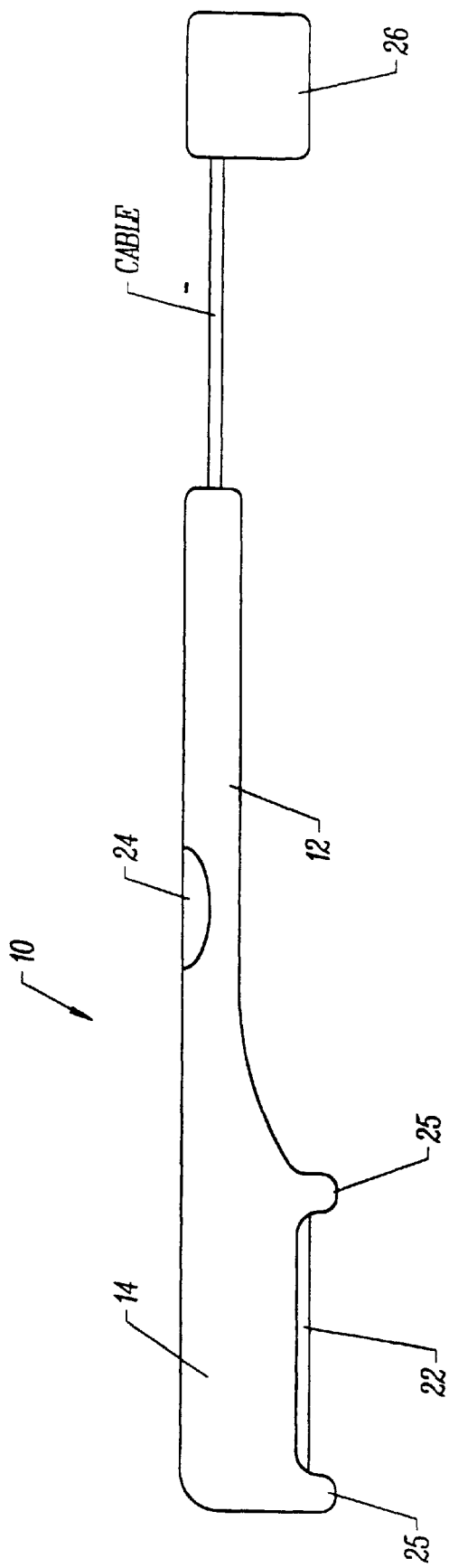

FIG. 1 is a perspective view of the apparatus of the present invention with a probe and two electrodes.

FIG. 2 is a perspective view of the apparatus of the present invention with a probe, an electrode positioned at a distal end of the probe and two electrodes positioned on opposite sides of an insulator.

FIG. 3 is a perspective view of a knee joint with chondromalacia.

FIG. 4 is a perspective view of the apparatus of FIG. 2 with a probe coiled distal end.

FIG. 5 is a perspective view of the apparatus of the present invention with two electrodes positioned on opposite sides of an insulator.

FIG. 6 is perspective view of the apparatus of the present invention including an electrode with radiused edges.

Figure 7:
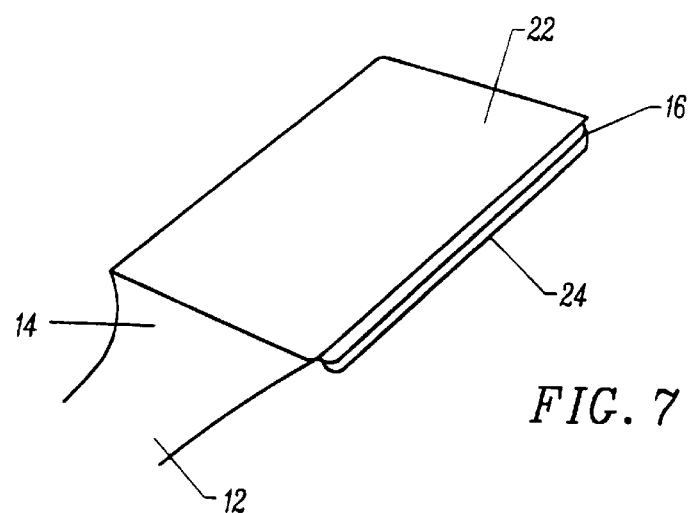

FIG. 7 is a perspective view of the apparatus of the present invention including a rectangularly shaped electrode.

Figure 8:
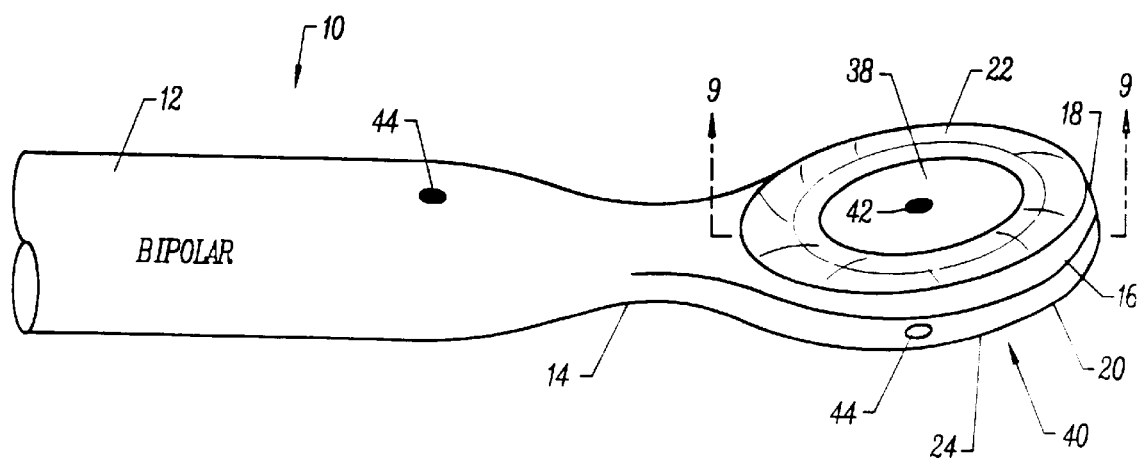

FIG. 8 illustrates a perspective view of the apparatus of the present invention with electrodes formed on peripheral faces of the insulator.

Figure 9:
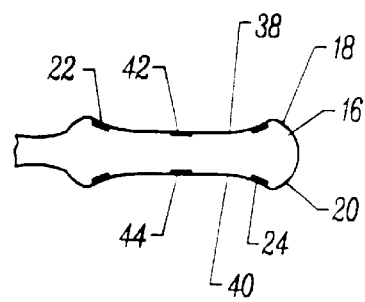

FIG. 9 is a cross-sectional view of the apparatus of FIG. 8 taken along the lines 9—9.

Figure 10:
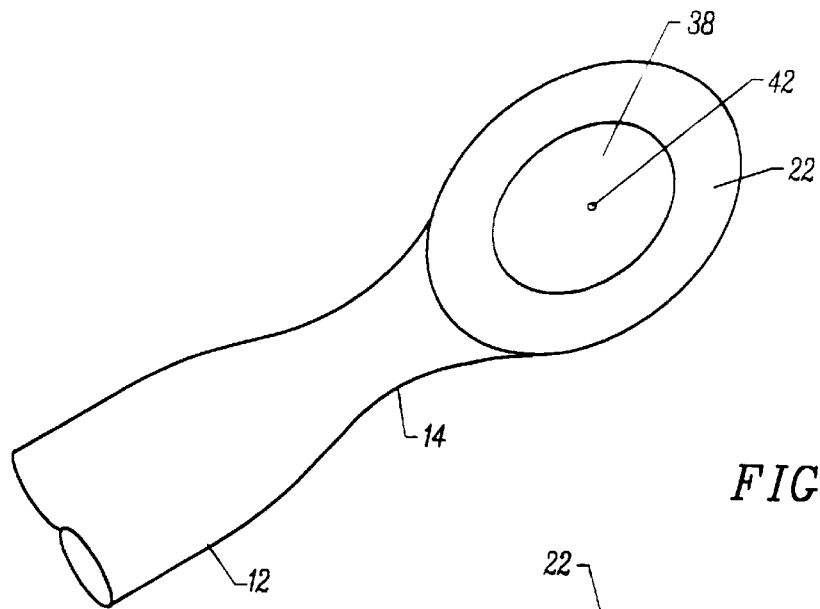

FIG. 10 is a perspective view of an electrode used with the apparatus of the present invention that is formed at a peripheral surface of the insulator and defines an interior non-conducting region.

Figure 11:
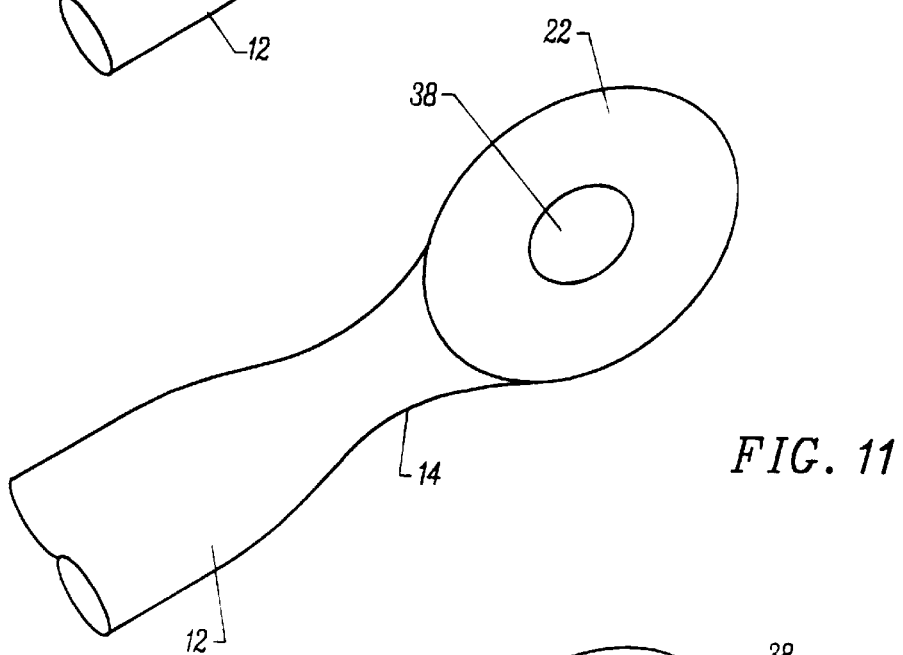

FIG. 11 is a perspective view of a toroidal electrode used with the apparatus of the present invention and defines an interior non-conducting region.

Figure 12:
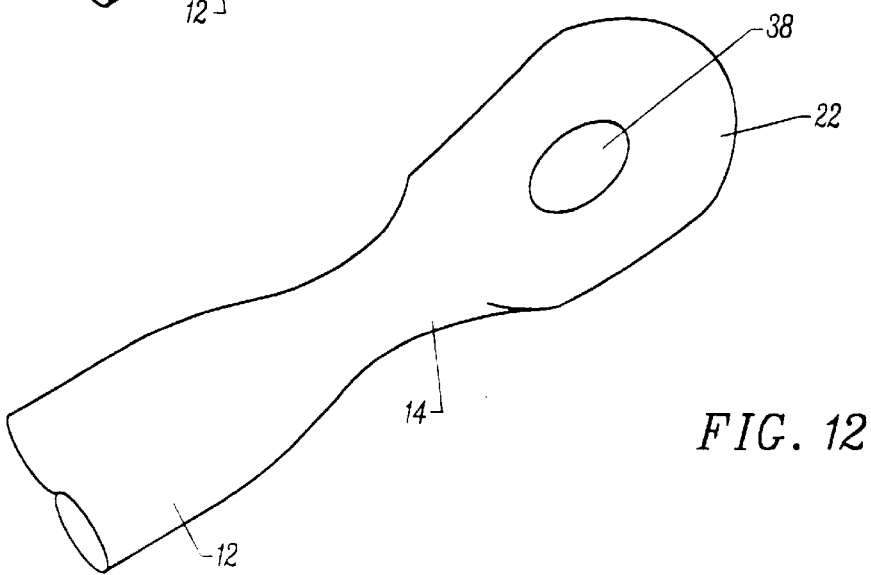

FIG. 12 is a perspective view of a non-circular toroidal electrode used with the apparatus of the present invention and defines an interior non-conducting region.

Figure 13:
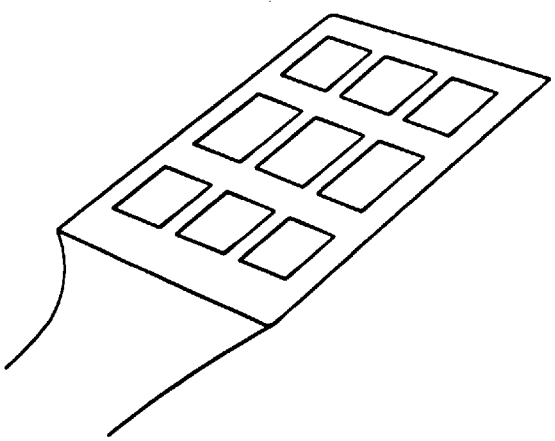

FIG. 13 is a perspective view of a segmented electrode used with the apparatus of the present invention.

Figure 14:
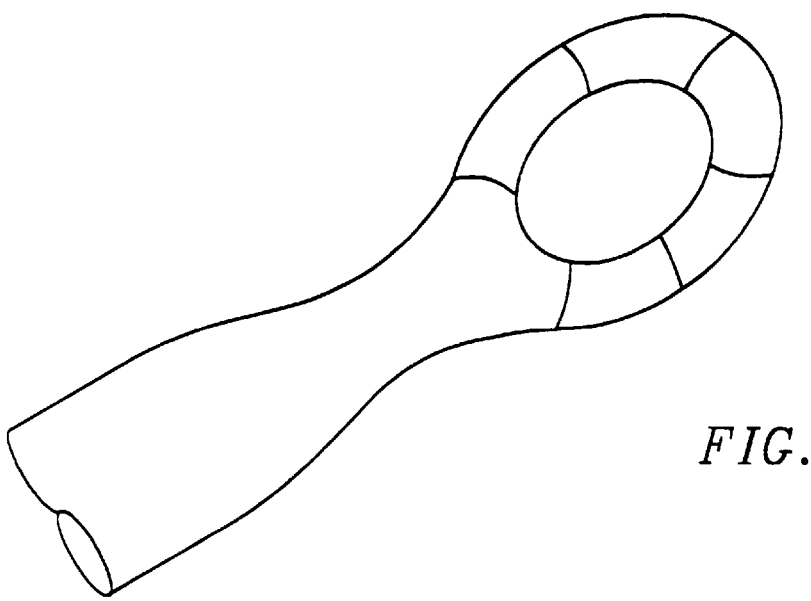

FIG. 14 is a perspective view of a segmented toroidal electrode used with the apparatus of the present invention.

Figure 15:
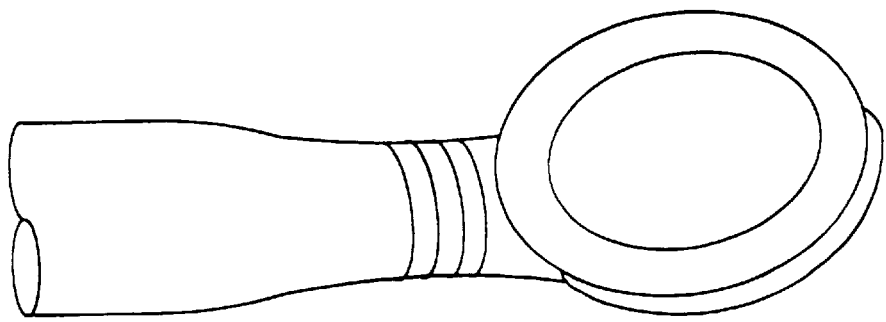

FIG. 15 is a perspective view of a flexible probe used with the apparatus of the present invention.

Figure 16:
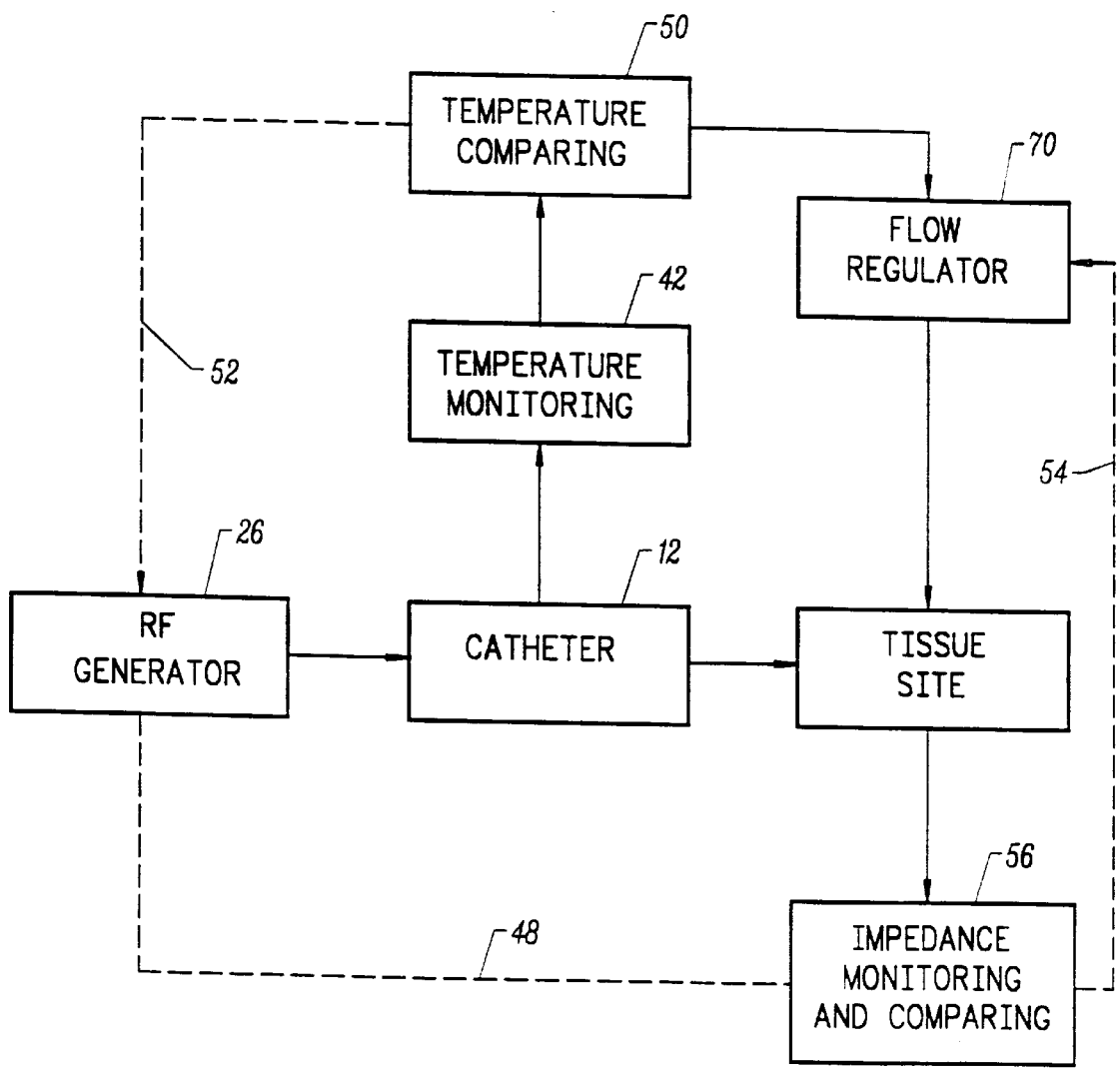

FIG. 16 is a block diagram illustrating a feedback system useful to control the temperature of electrodes of the present invention.

Figure 17:
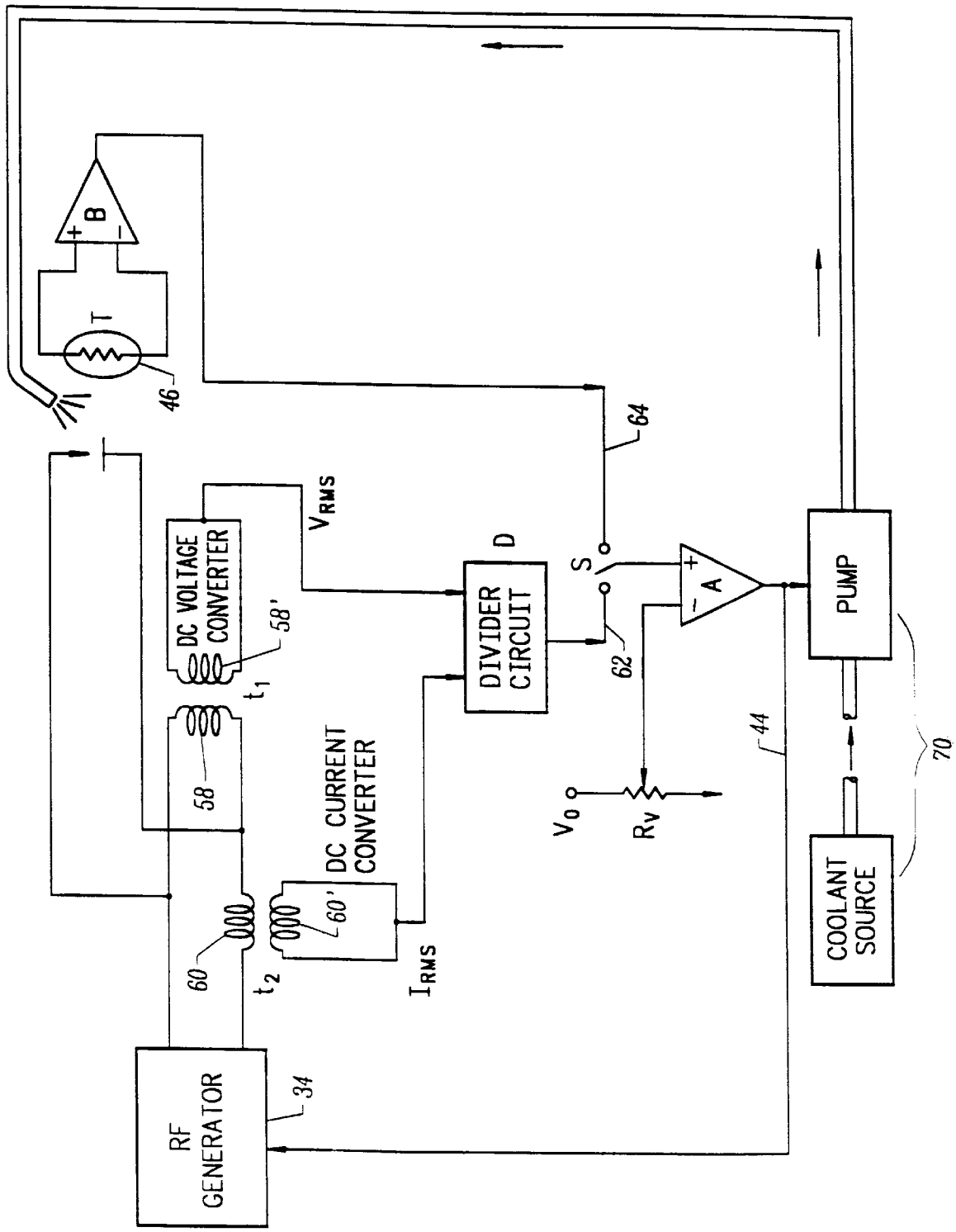

FIG. 17 illustrates a circuit useful to implement the feedback system of FIG. 16.

Figures 18A, 18B:
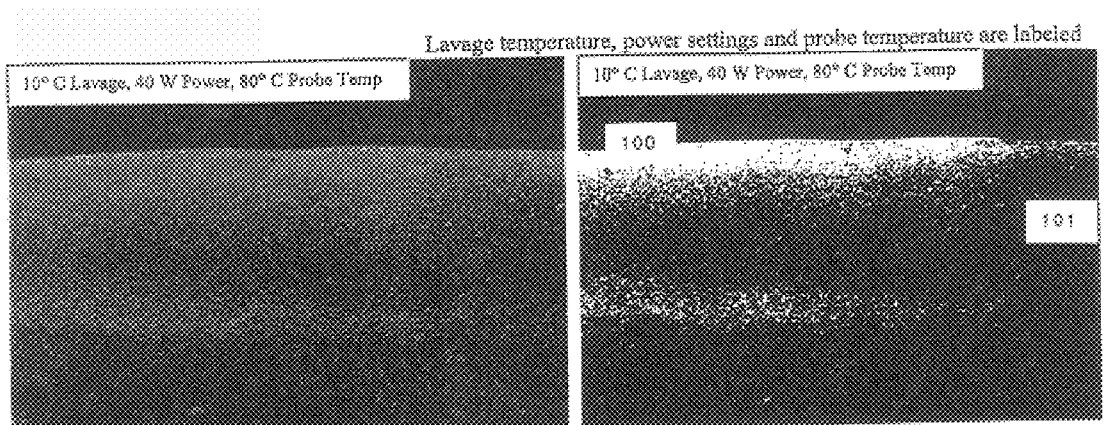

FIGS. 18A–18B illustrate two views of results obtained at 10° C. Lavage, 40 watts and an 80° C. probe temperature, representing an embodiment of the invention.

Figures 19A, 19B:
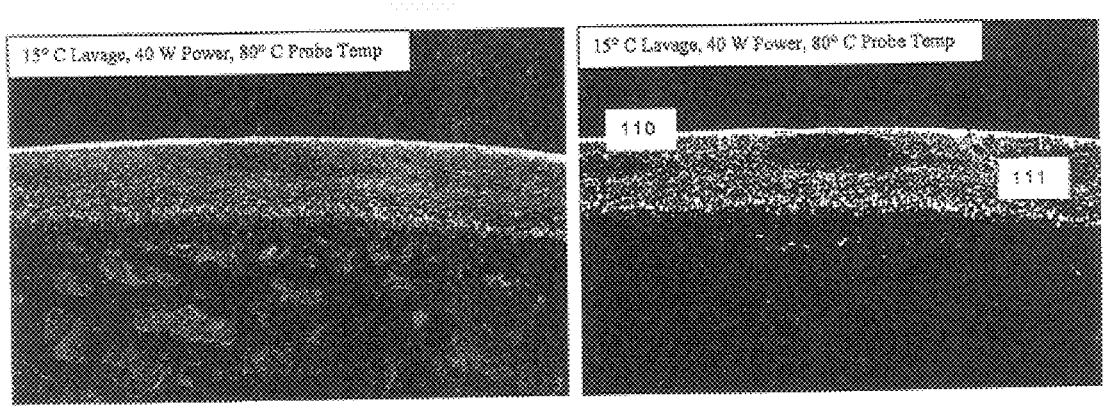

FIGS. 19A–19B illustrate two views of results obtained at 15° C. Lavage, 40 watts and an 80° C. probe temperature, representing an embodiment of the invention.

Figures 20A, 20B:
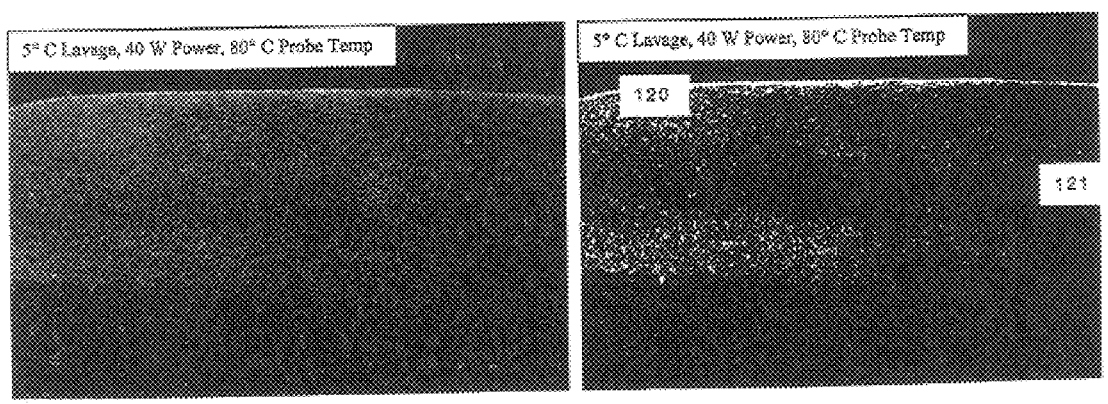

FIGS. 20A–20B illustrate two views of results obtained at 5° C. Lavage, 40 watts and an 80° C. probe temperature, representing an embodiment of the invention.

Figure 21A:
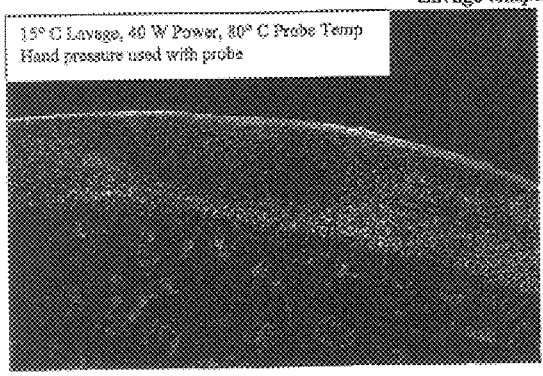
Figure 21B:
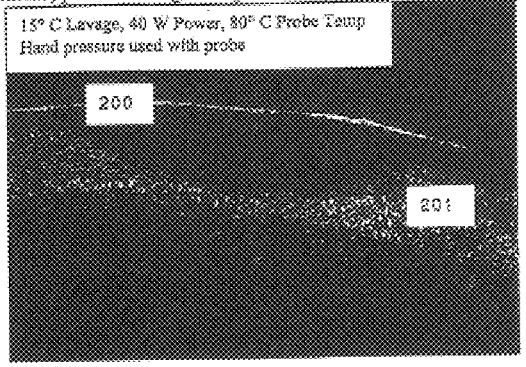

FIGS. 21A–21B illustrate two views of results obtained at 15° C. Lavage, 40 watts and an 80° C. probe temperature, representing an embodiment of the invention.

Figure 22A:
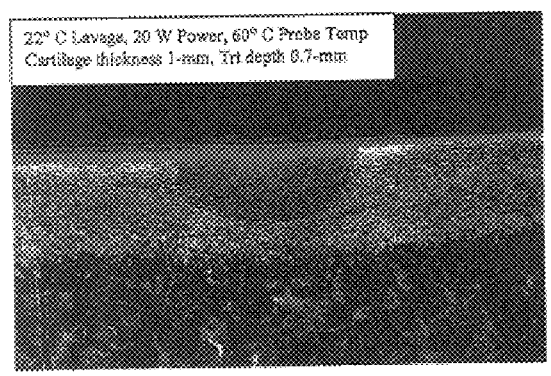
Figure 22B:
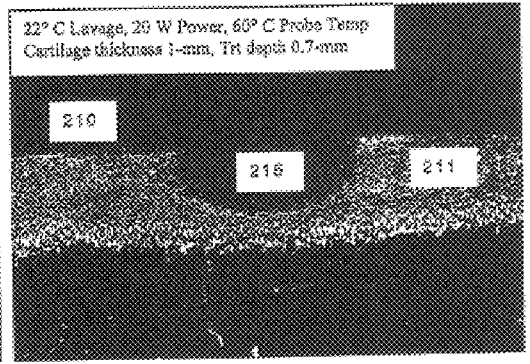

FIGS. 22A–22B illustrate two views of results obtained at 22° C. Lavage, 20 watts and a 60° C. probe temperature, representing an embodiment of the invention.

Figure 23A:
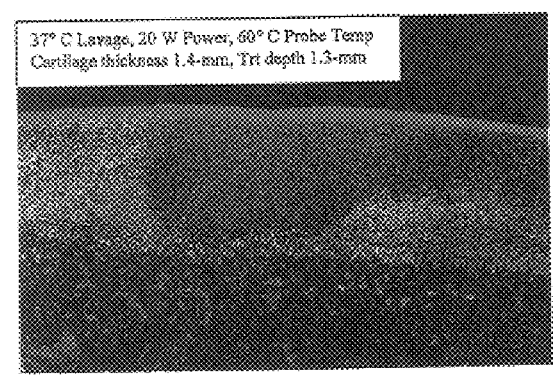
Figure 23B:
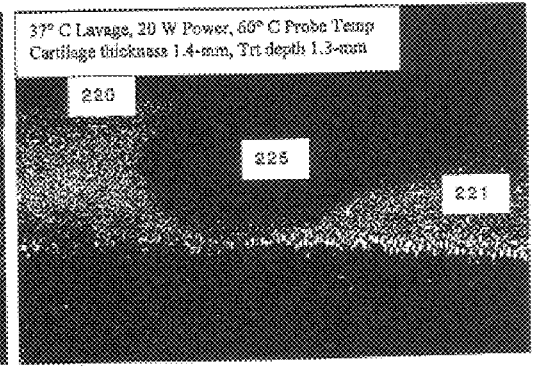

FIGS. 23A–23B illustrate two views of results obtained at 37° C. Lavage, 20 watts and a 60° C. probe temperature, representing an embodiment of the invention.

DETAILED DESCRIPTION

As shown in FIG. 1, a thermal energy delivery apparatus 10 is configured to be positioned adjacent to, but spaced apart from a joint surface. Included is a probe 12 with a distal end 14, a first electrode 22 and a second electrode 24. Electrodes 22 and 24 can be operated in bipolar or monopolar. Bipolar is preferred. A distancing element 25 distances a thermal energy delivery surface of electrode 22 from the joint surface. Preferably, the thermal energy delivery surface of electrode 22, or of electrode 24, does not touch the joint surface. As illustrated in FIG. 1, distancing element 25 is included. In other embodiments, distancing element 25 is not included and the thermal energy delivery surface of electrode 22 or of electrode 24 are positioned directly on the joint surface.

Referring now to FIG. 2, thermal energy delivery apparatus 10 is configured to be positioned and deliver thermal energy to a joint surface. Apparatus 10 includes probe 12 with distal end 14 and an insulator 16 including first and second surfaces 18 and 20 formed on opposite sides on insulator 16. A pair of electrodes are also provided. First electrode 22 is positioned on first surface 18 of insulator 16. Second electrode 24 is positioned on second surface 20 of insulator 16. Thermal energy source 26 is coupled to first electrode 22 and second electrode 24 with a cable.

Insulator 16 can be an elongated structure with a longitudinal axis. Surfaces 18 and 20 can be parallel to each other. Insulator can be made of a variety of insulating materials known to those skilled in the art. Insulator 16 need not be one integral ilit and surfaces 18 and 20 can be made of separate insulators that are separated. Surfaces 18 and 20 can be planar, non-planar and have geometries that conform closely to interior joint surfaces. In one embodiment, the dimensions of distal end 14 are sufficiently small to be positioned on a joint surface.

A knee joint surface 28 is shown in FIG. 3. Knee joint surface 28 is defined by a first cartilage bed 30 formed at a distal end of the femur, and a second cartilage bed 32 formed at a distal end of the tibia. The present invention is not limited to the knee joint surface and can be used in a variety of different joint surfaces. Any joint surface susceptible to chondromalacia is treatable with apparatus 10. The present invention is suitable for the treatment of fibrillated cartilage joint surfaces to reduce the level of fibrillation and create smoother surfaces. The present invention is also used to treat irregular joint surfaces, where there are peaks and valleys, and create a less irregular joint surface. In certain embodiments, the irregular joint surface becomes a smooth joint surface.

A first plurality of cartilage strands 34 are coupled to first cartilage bed 30 and have become dislodged and dangle in joint surface 28. A second plurality of cartilage strands 36 are connected to second cartilage bed 32.

Second plurality of cartilage strands 36 have also become dislodged and dangle in joint surface 28.

In one embodiment of the invention, a method is provided that modifies a geometry of a fibrillated cartilage surface. Sufficient thermal energy is delivered from first electrode 22 or second electrode 24 at different times to reduce a level of fibrillation of the fibrillated cartilage joint surface. In various embodiments of the invention, sufficient thermal energy is delivered electrode 22 or 24 to, (i) change the fibrillated cartilage surface to a smooth or smoother surface, (ii) reduce a level of fibrillation of the fibrillated cartilage surface, (iii) cause at least a portion of a plurality of cartilage strands coupled to the fibrillated cartilage surface to create a smoothened cartilage surface, (iv) cause at least a portion of a plurality of cartilage strands coupled to the fibrillated cartilage surface to melt onto the fibrillated cartilage surface or (v) melt at least a portion of a plurality of cartilage strands to create a smoothened cartilage surface.

First electrode 22 has a first thermal energy delivery surface configured to deliver thermal energy to cartilage strands 34 and second electrode 24 has a second thermal energy delivery surface configured to deliver thermal energy to cartilage strands 36. Thermal energy includes but is not limited to RF, microwave, resistive heating, ultrasound, coherent or incoherent light and a thermal jet source. By delivering the appropriate amount of thermal energy to joint surface 28, strands 34 and 36 move out of joint surface 28 and the surfaces of cartilage beds 30 and 32 are smoothened. Additionally, delivered thermal energy can remove some or substantially all of cartilage strands 34 and 36 from joint surface 28. The delivery of thermal energy physically smoothes the surface of cartilage beds 30 and 32, changes the ultrastructure of the cartilage, stimulates cartilage replication and growth and changes the chemical environment in joint surface 28 and cartilage beds 30 and 32 to relieve pain.

Apparatus 10 is used to modify the geometry of cartilage strands 34 and 36 through cartilage shrinkage and possibly limited ablation of strands 34 and 36. Distal end 14 of probe 12 is inserted through an arthroscope to joint surface 28. First and second electrodes 22 and 24 are introduced into joint surface 28. Sufficient thermal energy is delivered from electrodes 22 and 24 to shrink at least a portion of cartilage strands 34 and 36, causing the strands to lie down on cartilage beds 30 and 32. The delivery of thermal energy to joint surface 28 results in an "ironing" of cartilage strands 34 and 36 onto cartilage beds 30 and 32.

Sufficient thermal energy is delivered from first and second electrodes 22 and 24 to shrink at least a portion of cartilage strands 34 and 36 without ablating more than 25% of cartilage beds 30 and 32. In one embodiment, sufficient energy is delivered by first and second electrodes 22 and 24 to raise the temperature of joint surface in the range of 45 to 90 degrees C, preferably 45 to 75 degrees C. and more preferably 50 to 70 degrees C. Maintenance of a suitable temperature, and the delivery of thermal energy to joint surface 28, is sufficient to cause strands 34 and 36 to become at least partially melted onto the cartilage joint surface while minimizing ablation of cartilage beds 30 and 32.

Insulator 26 and first and second electrodes 22 and 24 are configured to be inserted into joint surface 28. Probe 12 is moved back and forth through joint surface 28 to deliver a sufficient amount of thermal energy to strands 34 and 36 to cause them to lie down on their respective cartilage beds. The thermal energy delivery surfaces of first and second electrodes 22 and 24 can move along the surfaces of cartilage beds 30 and 32 to complete the ironing effect.

Referring now to FIG. 4, distal end 14 of probe 12 can have a coiled geometry as well as a variety of geometric configurations. Preferably, distal end 14 is malleable or sufficiently flexible to impart movement of first and second electrodes 22 and 24. Distal end 14 can pivot, be hinged, be articulated, or made of a shaped memory metal, and the like, in order to enable first and second electrodes 22 and 24 to follow the contours of joint surface 28.

As shown in FIG. 5, first and second electrodes 22 and 24 can be operated in a bipolar mode. This concentrates the flow of RF energy between first and second electrodes 22 and 24 and diverts direct RF energy flow away from cartilage beds 30 and 32. RF energy which is directed between first and second electrodes 22 and 24 heats up fluids within joint surface 28 and provides a more controlled delivery of energy to cartilage strands 34 and 36. RF ablation of cartilage beds 30 and 32 is reduced.

First and second electrodes 22 and 24 can have a variety of different geometric configurations. As illustrated in FIG. 6, first and second electrodes 22 and 24 are symmetrically shaped with radiused edges. Elimination of sharp edges at an electrode surface reduce the creation of hot spots of thermal energy delivered to a site. In FIG. 7, first and second electrodes 22 and 24 have rectangular geometries with non-radiused edges. First and second electrodes 22 and 24 can each have different sizes and geometries. First and second electrodes 22 and 24 can be mirror images of each other or they can be different.

Referring now to FIG. 8, first and second electrodes 22 and 24 are formed on a periphery of insulation surfaces 18 and 20 respectively. In this embodiment, each electrode 22 and 24 defines a first and a second nonconducting region 38 and 40 on an insulator surface 18 and 20 within an interior of first and second electrodes 18 and 20. Non-conducting regions 38 and 40 can be the actual surface of insulator 16, or may be additional structures, each with a non-conducting surface that are formed on insulation surfaces 18 and 20. First and second sensors 42 and 44 can be provided and associated with first and second electrodes 22 and 24 to measure temperature and/or impedance.

First and second sensors 42 and 44 are positioned on a surface of first and second electrodes 22 and 24, on a surface of probe 12, on non-conducting regions 38 and 40, or can be advanced and retracted from distal end 14 to and from joint surface 28.

First and second sensors 42 and 44 are of conventional design, including but not limited to thermistors, thermocouples, resistive wires, and the like. Suitable thermal sensors 42 and 44 include a T type thermocouple with copper constantene, J type, E type, K type, fiber optics, resistive wires, thermocouple IR detectors, and the like. Sensors 42 and 44 need not be thermal sensors.

Sensors 42 and 44 measure temperature and/or impedance to permit monitoring and a desired level of energy delivered determined This reduces ablation damage to cartilage beds 30 and 32. If at any time sensor 42 or 44 determines that a desired temperature is exceeded, then an appropriate feedback signal is received at thermal energy source 26 which then regulates the amount of energy delivered to first and second electrodes 22 and 24.

Sensors 42 and 44 are positioned on non-conducting regions 38 and 40 in FIG. 9. Non-conducting regions 38 and 40 have a variety of geometric surfaces including but not limited to planar, non-planar, concave, convex, and the like. In one embodiment, non-conducting regions 38 and 40 are closer to the midline of insulator 16 than first and second electrodes 22 and 24. This enhances the bipolar conduction of thermal energy between electrodes 22 and 24 in the bipolar mode of operation.

First and second electrodes 22 and 24 can have various geometries including but not limited to cylindrical, semi-cylindrical, rectangular, cubic, irregularly shaped, toroidal (FIG. 10), non-circular toroidal (FIG. 11), nonsymmetrical, non-symmetrical toroidal (FIG. 12) or be segmented and capable of multiplexing (FIGS. 13 and 14). In one embodiment, first electrode 22 has a toroidal geometry, first sensor 42 is positioned on non-conducting region 38, and distal end 14 is flexible and curved.

FIG. 16 illustrates a block diagram of a temperature/impedance feedback system useful with apparatus 10. Thermal energy is delivered to first and second electrodes 22 and 24 by thermal energy source 26, and applied to cartilage strands 34 and 36. A monitor 56 ascertains tissue impedance, based on the energy delivered to tissue, and compares the measured impedance value to a set value. If the measured impedance exceeds the set value a disabling signal 48 is transmitted to thermal energy source 26, ceasing further delivery of thermal energy to first and second electrodes 22 and 24. If measured impedance is within acceptable limits, energy continues to be applied. During the application of thermal energy to cartilage strands 34 and 36, sensor 42 measures the temperature at the surface of sensor 42. A comparator 50 receives a signal representative of the measured temperature and compares this value to a pre-set signal representative of the desired temperature. Comparator 50 sends a signal to thermal energy source 26 to continue sending thermal energy, to increase or decrease the level of delivered thermal energy, or to cease delivery of thermal energy.

An output 52 from temperature comparator 50 can be input to thermal energy source 26 to regulate the amount of power delivered. Output 54 from impedance monitor 56 can be input control the temperature at joint surface 28.

Referring now to FIG. 17, thermal energy source 26 is coupled to first and second electrodes 22 and 24 and apply a biologically safe voltage to cartilage strands 34 and 36. In the embodiment illustrated in FIG. 11, apparatus 10 is represented as a bipolar ablation device. First and second electrodes 22 and 24 are connected to a primary side of transformer windings 58 and 60. The common primary windings 58 and 60 are magnetically coupled with a transformer core to secondary windings 58' and 60'.

The primary windings 58 of the first transformer $t_1$ couple the output voltage of apparatus 10 to the secondary windings 58'. The primary windings 60 of the second transformer $t_2$ couple the output current of ablation apparatus 10 to the secondary windings 60'.

Measuring circuits determine the root mean square (RMS) values or magnitudes of the current and voltage. These values, represented as voltages, are inputted to a diving circuit D to geometrically calculate, by dividing the RMS voltage value by the RMS current value, the impedance of the tissue site at sensor 42.

The output voltage of the divider circuit D is presented at the positive (+) input terminal of comparator A. A voltage source $V_o$ supplies a voltage across the variable resistor $R_v$, thus allowing one to manually adjust the voltage presented at the negative input of comparator A. This voltage represents a maximum impedance value beyond which power will not be applied to electrode 22. Specifically, once the tissue is heated to a temperature corresponding to an impedance value greater than the maximum cut-off impedance, thermal energy source 26 stops supplying energy to first and second electrodes 22 and 24. Comparator A can be of any of a commercially available type that is able to control the amplitude or pulse width modulation of thermal energy source 26.

The temperature within joint surface 28 can be controlled based on the tissue impedance, as represented by signal 62, or based on tissue temperature, as represented by signal 64. In one embodiment, the switch S is activated to allow the impedance signal 62 to enter the positive (+) input terminal of comparator A. This signal along with the reference voltage applied to the negative (−) input terminal actuates comparator A to produce an output signal. If the selected tissue ablation site is heated to a biologically damaging temperature, the tissue impedance will exceed a selected impedance value seen at the negative (−) input terminal, thereby generating disabling signal 48 to disable thermal energy source 26, ceasing the energy supplied to first and second electrodes 22 and 24.

The output signal of comparator A may either disable thermal energy source's 26 energy output, depending on the tissue temperature as reflected by its impedance.

The thermal energy source 26 of apparatus 10 may also be used in combination with pre-cooling system 70 comprising a coolant source and a pump. The pre-cooling system 70 can be used to Lavage the joint with an irrigating solution which has been placed into a freezer or refrigerator to be chilled at or below 0° C. before use in the surgical procedure. The irrigating solution lowers the joint surface and target tissue temperature for treatment below the typical body temperature of 37° C. Temperature sensor 46 is used to monitor the temperature of the tissue in the surgical field.

Because the entire surgical field is subjected to the irrigating solution, the pre-cooled thermal environment provides protection from collateral damage to non-targeted tissue. As thermal energy is applied from RF generator 34 to the primary winding 58 in the electrode of the apparatus, a thermal gradient is formed as the apparatus is placed near the joint surface for treatment. The thermal energy heats the joint surface and target tissue for a pre-determined amount of time to produce a desired ablation effect on the cartilage strands of the joint surface to smooth the surface during treatment. The targeted tissue strands are heated and ablated with reduced thermal effect on the underlying non-targeted joint surface. Thus, the chondrocytes in the articular cartilage surface remain viable and are minimally affected by the thermal energy from the apparatus during a surgical procedure.

FIGS. 18A–23B illustrate the in vitro studies of apparatus 10 utilizing a pre-cooling system 70 as shown in FIG. 17. All of the treated tissues shown in FIGS. 18A–23B were treated to substantially the same level of smoothness. All of the images shown in FIGS. 18A–23B at depicted at substantially the same magnification. The term approximately, as used herein, is defined as at least close to a given value (e.g., preferably within 10% of, more preferably within 1% of and most preferably within 0.1% of). The term substantially, as used herein, is defined as at least approaching a given state (e.g., preferably within 10% of, more preferably within 1% of, and most preferably within 0.1% of). The term coupled, as used herein, is defined as connected, although not necessarily directly, and not necessarily mechanically.

FIGS. 18A–B illustrate a treatment with an irrigating solution at a temperature of approximately 10° C. FIG. 18A is a color microscopic cross-section of the articular cartilage surface 100 after pre-cooling treatment while FIG. 18B is a black and white representation for reference. The probe velocity was 1 mm/sec and applied with a motorized apparatus. Cell death is indicated by red with some staining artifacts remaining. As indicated, the irrigating solution was cooled to 10° C. under 40 W of power and a probe temperature of 80° C. The underlying articular cartilage bed 101 shows minimal cell death after thermal energy application along tissue surface 100 during treatment wherein viable chondrocytes are unaffected by the probe apparatus.

FIGS. 19A–B illustrate a treatment with an irrigating solution at a temperature of approximately 15° C. FIG. 19A is a color microscopic cross-section of the articular cartilage surface 110 after pre-cooling treatment while FIG. 19B is a black and white representation for reference. The probe velocity was 1 mm/sec and applied with a motorized apparatus. As indicated, the irrigating solution was cooled to 15° C. under 40 W of power and a probe temperature of 80° C. The underlying articular cartilage bed 111 shows minimal cell death along treated cartilage surface 100.

FIGS. 20A–B illustrate a treatment with an irrigating solution at a temperature of approximately 5° C. FIG. 20A is a color microscopic cross-section of the articular cartilage surface 120 after pre-cooling treatment while FIG. 20B is a black and white representation for reference. The probe velocity was 1 mm/sec and applied with a motorized apparatus. As indicated, the irrigating solution was cooled to 5° C. under 40 W of power and a probe temperature of 80° C. The underlying articular cartilage bed 121 shows minimal cell death along treated cartilage surface 120.

FIGS. 21A–B illustrate a treatment with an irrigating solution at a temperature of approximately 15° C. FIG. 21A is a color microscopic cross-section of the articular cartilage surface 200 after pre-cooling treatment while FIG. 21B is a black and white representation for reference. Hand pressure was used on the probe apparatus to test if physical insult and pressure in addition to the application of thermal energy to the target joint surface tissue would result in greater cell death to non-targeted tissue. As the hand pressure was increased on the articular cartilage surface 200, cell death due to physical pressures occurred as indicated by the central darkened zone with red stain. The irrigating solution was cooled to 15° C. under 40 W of power with a probe temperature of 80° C. However, since the joint and surgical field was pre-cooled, the non-targeted tissue 201 beyond where the physical pressure was applied to the articular cartilage illustrates protection from the thermal effect of the probe.

FIGS. 22A–B illustrate a treatment with an irrigating solution at a room temperature of approximately 22° C. FIG. 22A is a color microscopic cross-section of the articular cartilage surface 210 while FIG. 22B is a black and white representation for reference. Power was reduced to 20 W while the probe temperature was reduced to 60° C. The probe velocity was 1 mm/sec and applied with a motorized apparatus. As the thermal energy was applied to the joint surface tissue 210, cell death occurred at both the treated surface 210 and below the tissue surface in area 215 of the articular cartilage 211 beyond the treatment area of articular cartilage surface 210.

FIGS. 23A–B illustrate a treatment with an irrigating solution at a body temperature of approximately 37° C. FIG. 23A is a color microscopic cross-section of the articular cartilage surface 220 while FIG. 23B is a black and white representation for reference. Power was reduced to 20 W while the probe temperature was reduced to 60° C. The probe velocity was 1 mm/sec and applied with a motorized apparatus. As the thermal energy was applied to the joint surface tissue 220, significant cell death occurred along the tissue surface 220 and beyond the treatment area of articular cartilage surface 220 over a greater area 225 of the articular cartilage 221 as shown by the red stain. As illustrated, a larger tissue cartilage depth and lower probe temperature and power showed a greater effect and cell death from thermal insult than pre-cooled tissues at higher probe temperatures and powers as shown in FIGS. 18–21.

The arthroscopic set up includes an irrigating system, a viewing system and a positioning system in addition to the normal equipment utilized in a less invasive procedure conducted under general anesthesia. The irrigating system involves a fluid (irrigant) source (typically two liter bags of normal or isotonic saline), connecting tubing to include tubing clamps for mechanically inhibiting and controlling the flow of the irrigating solution, the percutaneous canula for insertion into the joint space to which the connecting tubing is attached providing the portal for irrigant supply, and a second portal or outflow port allowing irrigating fluid to exit the joint capsule which may have an extension tube to direct the outflow of the irrigant away from the operator. The irrigating solutions are commonly stored in the operating room and are then used at (room) stored temperature.

Either (or both) of these canulas may be incorporated into a canula system allowing the introduction of a "scope" (rod lens apparatus for viewing the interior of the joint space) or the introduction of all manner of interventional tools, to include probe cutters, electrosurgical and electrothermal instruments. Some surgeons utilize a pump system that senses intra-articular pressure and adequate hemostasis. Otherwise, the intra-articular (oint capsule) pressure is generated by elevating the solution bags above the level of the patient making use of a simple gravity supply.

The viewing system includes the arthroscopic "scope" (optical rod lens) to which is typically attached a clip on video camera that feeds a video signal to the camera base and a CRT monitor for viewing.

In experimental studies utilizing osteochondral specimens in a bovine model, significant protection against chondrocyte death was observed following precooling of the tissues to approximately 5° C. Protection against chondrocyte death was also observed following precooling of the tissues to approximately 10° C. and approximately 15° C. Slight protection was even observed following precooling of the tissues to merely approximately 22° C., compared to the results obtained at approximately 37° C. In specimens that were not sufficiently precooled, cell death up to and including the full thickness of the cartilage treated and the underlying subchondral bone was observed when the superficial cartilage was thermally treated. These studies demonstrate that thermal sealing of the surface can be achieved with minimal cell death in the underlying cartilage.

A positioning system is selected, based upon the anatomy to be addressed with each procedure that is designed to immobilize or suspend the surgical site to facilitate the physician's access to the surgical field.

A preferred embodiment utilizes the standard arthroscopic system with the following modifications. The irrigating solution can cooled significantly by placing the solutions in a freezer or refrigerator. Because Normal Saline and Lactated Ringers Solution contain salts and sugars in solution they can be chilled to temperatures at or below 0° C. without the concern of the solution freezing or forming crystals.

The invention can include the use of a subsystem including an irrigating solution reservoir coupled to a heat exchanger. The solution in the reservoir can thus be delivered to the non-targeted tissue at any temperature at any time, during even a lengthy procedure.

The invention can also utilize data processing methods that transform signals from solution to control the temperature of the solution. For example, the invention can be combined with instrumentation to obtain state variable information to actuate interconnected discrete hardware elements. For instance, the operation of the reservoir heat exchanger subsystem can be controlled by the use of one, or more, set point(s) in conduction with an algorithm. The algorithm can gather state variable data such as a deviation of the temperature of the irrigating solution in the reservoir from the set point(s) and dynamic data such as the rate of change of the temperature of the irrigating solution in the reservoir. The algorithm can transform the set point(s), the state variable data and/or the dynamic data the into control signals that actuate the heat exchanger to control the temperature of the solution (e.g., start a pump in the heat exchanger to lower the temperature of the solution in the reservoir).

The invention can also be included in a kit. The kit can include some, or all, of the components that compose the invention. More specifically, the kit can include the probe, conduits for providing the solution to the non-targeted tissue and other components of the invention. The kit can also include the solution. The kit can also contain instructions for practicing the invention and apparatus for carrying out the invention. Unless otherwise specified, the components (and apparatus and/or instructions) of the kit can be the same as those used in the invention.

The cooled solution is used to "Lavage" the joint capsule for several minutes during the initial visual examination upon entering the joint before performing an intervention that will utilize a thermal device. Temperature of the solution exiting the outflow port can be monitored to assess the superficial intra-articular temperature by comparing the temperature of the in-flow irrigant with the temperature of the out-flow irrigant at low flow rates. In this way, the temperature of the tissues in the joint capsule and the tissues up to a centimeter away from the joint capsule can be cooled significantly.

Cooling the tissues in this way sets up a thermal gradient that offsets the thermal influence of the intervention. Both targeted and non-targeted tissues are cooled requiring an adjustment of the thermal probe accordingly and allowing for the use of higher temperatures spread away from the target area. The goal is to prevent temperature elevations in non-targeted tissues from exceeding 44° C. above which cell death occurs. In addition, since procedures in the peripheral joints and in particular in the knee, utilize a tourniquet system to control bleeding, the normal warming effects of vascularized tissue can be negated when the tourniquet is employed and greater cooling can be achieved that persists for a longer period of time. There are no untoward effects of cooling these ligamentous and bony structures to near freezing temperatures for a limited period of time.

The invention provides for the virtual elimination of thermal insult when compared to approaches that take no thermal defensive measures. The invention has the added benefit of greater heamostasis control even when a tourniquet is employed and even in the face of higher patient blood pressure.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A method for treating tissue in an arthroscopic environment, comprising the steps of precooling the arthroscopic environment and adjacent structures, providing a thermal energy delivery device including a probe with a distal end, a proximal end and a thermal energy delivery surface, providing a thermal energy source coupled to the thermal energy delivery surface, positioning the thermal energy delivery surface adjacent to a targeted tissue surface and delivering sufficient thermal energy from the thermal energy delivery surface to modify at least a portion of the targeted tissue surface, the precooling step being discontinued before the commencement of the delivering step.

2. The method of claim 1, wherein the precooling is accomplished by an irrigating solution selected from liquids consisting of normal saline, ringers lactated solution, Glycine, and bacteriostatic water.

3. The method of claim 2, wherein the irrigating solution is cooled to a temperature between approximately 20° C. and approximately −5° C.

4. The method of claim 1, wherein the probe is heated to a temperature of greater than approximately 50° C.

5. The method of claim 4, wherein the temperature is between approximately 60° and approximately 90° C.

6. The method of claim 4, wherein the probe delivers monopolar RF energy mediated by an electrothermal generator.

7. The method of claim 4, wherein the probe delivers bipolar RF energy mediated by a radiofrequency generator.

8. The method of claim 4, wherein the probe delivers optical energy.

9. The method of claim 4, wherein the probe delivers ultrasonic energy.

10. The method of claim 4, wherein the probe delivers resistive or conductive thermal energy.

11. The method claim 4, wherein the probe delivers thermal energy by means of a heated liquid.

12. The method of claim 4, wherein the probe delivers microwave energy.

13. A method of protecting non-targeted tissues in an arthroscopic environmrent, comprising the steps of precooling the arthroscopic environment and adjacent structures by means of an irrigating solution selected from liquids consisting of normal saline, ringers lactated solution, Glycine, and bacteriostatic water, the composition of the irrigating solution being modified to lower a freezing point by the addition of at least one substance that effects a decrease in the freezing point and is selected from the group consisting of glycine, glucose and electrolyte, providing a thermal energy delivery device including a probe with a distal end, a proximal end and a thermal energy delivery surface, providing a thermal energy source coupled to the thermal energy delivery surface, positioning the thermal energy delivery surface adjacent to a targeted tissue surface and delivering sufficient thermal energy from the thermal energy delivery surface to modify at least a portion of the targeted tissue surface.

14. A method for treating tissue within an arthroscopic environment, comprising the steps of precooling the arthroscopic environment and adjacent structures, providing a thermal energy delivery device including a probe with a distal end, a proximal end and a thermal energy delivery surface, providing a thermal energy source coupled to the thermal energy delivery surface, positioning the thermal energy delivery surface adjacent to an articular joint lining and delivering sufficient thermal energy from the thermal energy delivery surface to reduce a level of fibrillation at a fibrillated cartilage surface.

15. The method of claim 14, wherein the probe is used to coagulate the fibrillated cartilage surface to cause shrinking and removal of fibrillated cartilage.

16. The method of claim 15, wherein the probe delivers monopolar RF energy mediated by an electrothermal generator.

17. The method of claim 15, wherein the probe delivers bipolar RF energy mediated by a radiofrequency generator.

18. The method of claim 15, wherein the probe delivers optical energy.

19. The method of claim 15, wherein the probe delivers ultrasonic energy.

20. The method of claim 15, wherein the probe delivers resistive or conductive thermal energy.

21. The method of claim 15 wherein the probe delivers a heated liquid.

22. The method of claim 15, wherein the probe delivers microwave energy.

23. The method of claim 14, wherein the probe is used to coagulate the fibrillated cartilage to cause sealing of the fibrillated cartilage surface.

24. The method of claim 14, wherein precooling is accomplished with a liquid irrigant used in arthroscopic surgery selected from the group consisting of normal saline, ringers lactated solution, Glycine, and bacteriostatic water.

25. The method of claim 14, wherein the precooling step includes the step of Aid as supplying the arthroscopic environment and adjacent structures with an irrigating solution cooled to temperatures less than approximately 20° C.

26. The method of claim 18, wherein the irrigating solution is modified to lower a freezing point by the addition of at least one substance that effects a decrease in the freezing point and is selected from the group consisting of glycine, glucose, and electrolyte.

27. The method of claim 14, wherein the probe is heated to a temperature of greater than approximately 50° C.

28. The method of claim 27 wherein the temperature is between approximately 60° and approximately 90 C.

29. An apparatus to protect non-targeted tissues in an arthros environment, comprising a thermal energy delivery device including a probe with a distal end, a proximal end and a thermal energy delivery surface, a thermal energy source coupled to the thermal energy delivery surface, a conduit for providing a cooling irrigating solution to the arthroscopic environment and a source of a cooling liquid coupled to the conduit, the liquid being modified to lower a freezing point by the addition of at least one substance that effects a decrease in the freezing point and is selected from the group consisting of glycine, glucose and electrolyte.

30. The apparatus of claim 24, wherein the liquid is selected from the group consisting of normal saline ringers lactated solution, Glycine and bacteriostatic water.

31. The apparatus of claim 29, wherein said source includes a reservoir and a heat exchanger coupled to the reservoir.

32. The apparatus of claim 29, wherein said source operates according to an algorithm that transforms data concerning the liquid into signals that control the temperature of the liquid.

33. A method for treating tissue in an arthroscopic environment having adjacent structures with a thermal energy delivery device having proximal and distal extremities with an electrode carried by the distal extremity and a thermal energy source coupled to the proximal extremity and the electrode, comprising the steps of precooling the arthroscopic environment and the adjacent structures, positioning the electrode adjacent to the targeted tissue and delivering thermal energy from the thermal energy source to the electrode to modify at least a portion of the targeted tissue, the precooling step being discontinued before the commencement of the delivering step whereby the precooling of the arthroscopic environment minimizes damage to the adjacent structures.

34. The method of claim 33, wherein the electrode is a radio frequency electrode and the thermal energy source is a radio frequency generator.

35. The method claim 35, wherein the delivering step includes the step of delivering radio frequency energy between the radio frequency electrode and a return electrode coupled to the radio frequency generator.

36. The method of claim 33, wherein positioning step includes the step of positioning the electrode adjacent to an articular joint lining.

37. The method of claim 36, wherein the delivering step includes the step of delivering sufficient thermal energy from the thermal energy source to the electrode to reduce a level of fibrillation at a fibrillated cartilage tissue.

38. A method for treating tissue in an arthroscopic environment having adjacent structures with a thermal energy delivery device having proximal and distal extremities with an electrode carried by the distal extremity and a thermal energy source coupled to the proximal extremity and the electrode, comprising the steps of precooling the arthroscopic environment and the adjacent structures, positioning the electrode adjacent to the targeted tissue and delivering thermal energy from the thermal energy source to the electrode to modify at least a portion of the targeted tissue, the delivering step including the step of delivering radio frequency energy between the radio frequency electrode and a return electrode coupled to the radio frequency generator and carried by the distal extremity of the thermal energy delivery device, whereby the precooling of the arthroscopic environment minimizes damage to the adjacent structures.

* * * * *

UNITED STATES PATENT AND TRADEMARK OFFICE
CERTIFICATE OF CORRECTION

PATENT NO. : 6,544,260 B1
DATED : April 8, 2003
INVENTOR(S) : Mark Markel, Hugh R. Sharkey and Gary S. Fanton It is certified that error appears in the above-identified patent and that said Letters Patent is hereby corrected as shown below:

Title page,
Item [56], References Cited, U.S. PATENT DOCUMENTS,
"300,155" reference, replace "1884" with -- 1894 --;
"3,595,239" reference, replace "Perersen" with -- Petersen --.
Please add the following omitted references:

| | | |
|---|---|---|
| -- 2,090,923 | 8/1937 | Wappler |
| 3,178,728 | 4/1965 | Christensen |
| 3,579,643 | 5/1971 | Morgan |
| 3,776,230 | 12/1973 | Neefe |
| 3,856,015 | 12/1974 | Iglesias |
| 3,867,728 | 2/1975 | Substad et al. |
| 3,879,767 | 4/1975 | Substad |
| 3,886,600 | 6/1975 | Kahn et al. |
| 3,938,198 | 2/1976 | Kahn et al. |
| 3,945,375 | 3/1976 | Banko |
| 3,987,499 | 10/1976 | Scharbach et al. |
| 3,992,725 | 11/1976 | Homsy |
| 4,043,342 | 8/1977 | Morrison, Jr. |
| 4,074,718 | 2/1978 | Morrison |
| 4,085,466 | 4/1978 | Goodfellow et al. |
| 4,129,470 | 12/1978 | Homsy |
| 4,134,406 | 1/1979 | Iglesias |
| 4,224,696 | 9/1980 | Murray et al. |
| 4,224,697 | 9/1980 | Murray et al. |
| 4,326,529 | 4/1982 | Doss et al. |
| 4,344,193 | 8/1982 | Kenny |
| 4,362,160 | 12/1982 | Hiltebrandt |
| 4,375,220 | 3/1983 | Matvias |
| 4,381,007 | 4/1983 | Doss |
| 4,397,314 | 8/1983 | Vaguine |
| 4,476,862 | 10/1984 | Pao |
| 4,483,338 | 11/1984 | Bloom et al. |
| 4,517,965 | 5/1985 | Ellison |
| 4,517,975 | 5/1985 | Garito et al. |
| 4,590,934 | 5/1986 | Malis et al. |
| 4,593,691 | 6/1986 | Lindstrom et al. |
| 4,597,379 | 7/1986 | Kihn et al. |
| 4,601,705 | 7/1986 | McCoy |
| 4,651,734 | 3/1987 | Doss et al. |
| 4,811,733 | 3/1989 | Borsanyi et al. |
| 4,815,462 | 3/1989 | Clark |
| 4,838,859 | 6/1989 | Strassmann |

UNITED STATES PATENT AND TRADEMARK OFFICE
CERTIFICATE OF CORRECTION

PATENT NO.    : 6,544,260 B1
DATED         : April 8, 2003
INVENTOR(S)   : Mark Markel, Hugh R. Sharkey and Gary S. Fanton It is certified that error appears in the above-identified patent and that said Letters Patent is hereby corrected as shown below:

Title page (cont'd),

| | | |
|---|---|---|
| 4,846,175 | 7/1989 | Frimberger |
| 4,873,976 | 10/1989 | Schreiber |
| 4,894,063 | 1/1990 | Nashef |
| 4,895,148 | 1/1990 | Bays et al. |
| 4,907,585 | 3/1990 | Schachar |
| 4,907,589 | 3/1990 | Cosman |
| 4,924,865 | 5/1990 | Bays et al. |
| 4,944,727 | 7/1990 | McCoy |
| 4,950,234 | 8/1990 | Fujioka et al. |
| 4,955,882 | 9/1990 | Hakky |
| 4,966,597 | 10/1990 | Cosman |
| 4,976,709 | 12/1990 | Sand |
| 4,976,715 | 12/1990 | Bays et al. |
| 4,998,933 | 3/1991 | Eggers et al. |
| 5,007,908 | 4/1991 | Rydell |
| 5,009,656 | 4/1991 | Reimels |
| 5,085,657 | 2/1992 | Ben-Simhon |
| 5,085,659 | 2/1992 | Rydell |
| 5,098,430 | 3/1992 | Fleenor |
| 5,100,402 | 3/1992 | Fan |
| 5,103,804 | 4/1992 | Abele et al. |
| 5,114,402 | 5/1992 | McCoy |
| 5,152,748 | 10/1992 | Chastagner |
| 5,178,620 | 1/1993 | Eggers et al. |
| 5,186,181 | 2/1993 | Franconi et al. |
| 5,191,883 | 3/1993 | Lennox et al. |
| 5,192,267 | 3/1993 | Shapira et al. |
| 5,201,729 | 4/1993 | Hertzmann et al. |
| 5,201,730 | 4/1993 | Easley et al. |
| 5,201,731 | 4/1993 | Hakky |
| 5,213,097 | 5/1993 | Zeindler |
| 5,230,334 | 7/1993 | Klopotek |
| 5,242,439 | 9/1993 | Larsen et al. |
| 5,242,441 | 9/1993 | Avitall |
| 5,261,906 | 11/1993 | Pennino et al. |
| 5,267,994 | 12/1993 | Gentelia et al. |
| 5,275,151 | 1/1994 | Shockey et al. |
| 5,279,559 | 1/1994 | Barr |
| 5,284,479 | 2/1994 | de Jong |

UNITED STATES PATENT AND TRADEMARK OFFICE
CERTIFICATE OF CORRECTION

PATENT NO. : 6,544,260 B1
DATED : April 8, 2003
INVENTOR(S) : Mark Markel, Hugh R. Sharkey and Gary S. Fanton It is certified that error appears in the above-identified patent and that said Letters Patent is hereby corrected as shown below:

Title page (cont'd),

| | | |
|---|---|---|
| 5,304,169 | 4/1994 | Sand |
| 5,308,311 | 5/1994 | Eggers et al. |
| 5,311,858 | 5/1994 | Adair |
| 5,320,115 | 6/1994 | Kenna |
| 5,323,778 | 6/1994 | Kandarpa et al. |
| 5,334,193 | 8/1994 | Nardella |
| 5,342,357 | 8/1994 | Nardella |
| 5,348,554 | 9/1994 | Imran et al. |
| 5,352,868 | 10/1994 | Denen et al. |
| 5,354,331 | 10/1994 | Schachar |
| 5,364,395 | 11/1994 | West, Jr. |
| 5,366,443 | 11/1994 | Eggers et al. |
| 5,366,490 | 11/1994 | Edwards et al. |
| 5,397,304 | 3/1995 | Truckai |
| 5,401,272 | 3/1995 | Perkins |
| 5,415,633 | 5/1995 | Lazarus et al. |
| 5,423,806 | 6/1995 | Dale et al. |
| 5,433,739 | 7/1995 | Sluijter et al. |
| 5,437,661 | 8/1995 | Rieser |
| 5,437,662 | 8/1995 | Nardella |
| 5,451,223 | 9/1995 | Ben-Simhon |
| 5,458,596 | 10/1995 | Lax et al. |
| 5,464,023 | 11/1995 | Viera |
| 5,465,737 | 11/1995 | Schachar |
| 5,484,403 | 1/1996 | Yoakum et al. |
| 5,484,432 | 1/1996 | Sand |
| 5,487,757 | 1/1996 | Truckai et al. |
| 5,498,258 | 3/1996 | Hakky et al. |
| 5,500,012 | 3/1996 | Brucker et al. |
| 5,507,812 | 4/1996 | Moore |
| 5,524,338 | 6/1996 | Martyniuk et al. |
| 5,527,331 | 6/1996 | Kresch et al. |
| 5,542,920 | 8/1996 | Cherif Cheikh |
| 5,569,242 | 10/1996 | Lax et al. |
| 5,599,356 | 4/1997 | Edwards et al. |
| 5,630,839 | 5/1997 | Corbett, III et al. |
| 5,681,282 | 10/1997 | Eggers et al. |
| 5,683,366 | 11/1997 | Eggers et al. |
| 5,697,909 | 12/1997 | Eggers et al. |
| 5,718,702 | 2/1998 | Edwards |
| 5,728,795 | 7/1998 | Bays |
| 5,810,809 | 8/1998 | Rydell --. |

UNITED STATES PATENT AND TRADEMARK OFFICE
CERTIFICATE OF CORRECTION

PATENT NO. : 6,544,260 B1
DATED : April 8, 2003
INVENTOR(S) : Mark Markel, Hugh R. Sharkey and Gary S. Fanton It is certified that error appears in the above-identified patent and that said Letters Patent is hereby corrected as shown below:

Title page (cont'd),
FOREIGN PATENT DOCUMENTS, please add the following:

| | | |
|---|---|---|
| -- Europe | 0257116 A1 | 3/1988 |
| Europe | 0274705 A1 | 7/1988 |
| Europe | 0479482 A1 | 4/1992 |
| Europe | 0479482 B1 | 5/1996 |
| Europe | 0521595 A2 | 1/1993 |
| Europe | 0542412 A1 | 5/1993 |
| Europe | 0558297 A2 | 9/1993 |
| Europe | 0566450 A1 | 10/1993 |
| Europe | 0572131 A1 | 12/1993 |
| Europe | 0682910 A1 | 11/1995 |
| Europe | 0729730 A1 | 9/1996 |
| Europe | 0737487 A2 | 10/1996 |
| Europe | 0783903 A1 | 7/1997 |
| France | 1122634 | 9/1956 |
| France | 2645008 | 3/1989 |
| Germany | DE3511107 A1 | 10/1986 |
| Germany | DE3632197 A1 | 3/1988 |
| Great Britain | 1340451 | 2/1973 |
| Great Britain | 2164473 | 3/1986 |
| Japan | JP 5-42166 | 5/1993 |
| PCT | WO 85/02762 | 7/1985 |
| PCT | WO 92/05828 | 4/1992 |
| PCT | WO 92/10142 | 6/1992 |
| PCT | WO 93/01774 | 2/1993 |
| PCT | WO 93/16648 | 9/1993 |
| PCT | WO 93/20984 | 10/1993 |
| PCT | WO 95/01814 | 1/1995 |
| PCT | WO 95/13113 | 5/1995 |
| PCT | WO 95/18575 | 7/1995 |
| PCT | WO 95/20360 | 8/1995 |
| PCT | WO 95/25471 | 9/1995 |
| PCT | WO 95/30373 | 11/1995 |
| PCT | WO 95/30377 | 11/1995 |
| PCT | WO 95/34259 | 12/1995 |
| PCT | WO 96/11638 | 4/1996 |
| PCT | WO 96/32051 | 10/1996 |
| PCT | WO 96/32885 | 10/1996 |
| PCT | WO 96/34559 | 11/1996 |
| PCT | WO 96/34568 | 11/1996 |

UNITED STATES PATENT AND TRADEMARK OFFICE
CERTIFICATE OF CORRECTION

PATENT NO. : 6,544,260 B1
DATED : April 8, 2003
INVENTOR(S) : Mark Markel, Hugh R. Sharkey and Gary S. Fanton It is certified that error appears in the above-identified patent and that said Letters Patent is hereby corrected as shown below:

Title page (cont'd),
| | | |
|---|---|---|
| PCT | WO 96/34571 | 11/1996 |
| PCT | WO 96/39914 | 12/1996 |
| PCT | WO 97/06855 | 2/1997 |
| PCT | WO 98/07468 | 2/1998 |
| PCT | WO 98/17190 | 4/1998 |
| USSR | 637118 | 12/1978 --. |

OTHER PUBLICATIONS, please add:
-- Trimedyne, The Less Invasive Laser Advantage, Omni Spinal Introduction System.

PRNewswire (Dec. 12, 1994), Two Physicians Perform First Outpatient Cervical Disc Procedure Using Laser Technology.

Introduction to the LDD Disc Kit, Oct. 16, 1996.

Mayer et al., Lasers in Percutaneous Disc Surgery: Beneficial Technology or Gimmick?, Vol. 25, No. 251 (1993), pp. 38-44.

Schatz et al., Preliminary Experience With Percutaneous Laser Disc Decompression in the Treatment of Sciatica, Vol. 38, No. 5, Oct. 1995, pp. 432-436.

Savitz M.A., Same-day Microsurgical Arthroscopic lateral-approach Laser-assisted (SMALL) Fluoroscopic Discectomy, Vol. 80, June 1994, pp. 1039-1045.

Bosacco et al., Functional Results of Percutaneous Laser Discectomy, Dec. 1996, pp. 825-828.

Sluijter M.E., The Use of Radiofrequency Lesions For Pain Relief in Failed Back Patients, Vol. 10, No. 1 (1998).

Cosman et al., Theoretical Aspects of Radiofrequency Lesions in the Dorsal Root Entry Zone, Vol. 15, No. 6 (1984), pp. 945-950.

Wilkins et al., Neurosurgery: Method of Making Nervous System Lesions, ch. 337, pp. 2490-2499.

Yonezawa et al., The System and Procedure of Percutaneous Intradiscal Laser Nucleotomy, Vol. 15, No. 5 (1990), pp. 1175-1185.

Kolarik et al., Photonucleolysis of Intervertebral Disc and it's Herniation (1990).

UNITED STATES PATENT AND TRADEMARK OFFICE
CERTIFICATE OF CORRECTION

PATENT NO. : 6,544,260 B1
DATED : April 8, 2003
INVENTOR(S) : Mark Markel, Hugh R. Sharkey and Gary S. Fanton It is certified that error appears in the above-identified patent and that said Letters Patent is hereby corrected as shown below:

Title page (cont'd),
Gottlob et al., LASERS IN SURGERY AND MEDICINE: Holmium: YAG Laser Ablation of Human Intervertebral Disc: Preliminary Evaluation, Vol. 12 (1991), pp. 86-91.

Buchelt et al., LASERS IN SURGERY AND MEDICINE: Fluorescence Guided Excimer Laser Ablation of Intervertebral Discs in Vitro, Vol. 11 (1991), pp. 280-286.

Choy et al., Percutaneous Laser Disc Decompression: A New Therapeutic Modality, Vol. 17, No. 8 (1992), pp. 949-956.

Sluijter et al., Persistant Pain, Modern Methods of Treatment: Treatment of Chronic Back and Neck Pain, Vol. 3 (1981), pp. 141-179.

Sluijter, INT DISABIL STUDIES: The Use of Radio Frequency Lesions for Pain Relief in Failed Back, Vol. 10, Sept. 4, 1996, pp. 37-43.

Shatz et al., CJS JCC Preliminary Experience with Percutaneous Laser Disc Decompression in the Treatment of Sciatica, Vol. 38, No. 5, Oct. 1995, pp. 432-436.

Gerber et al., DER ORTHOPADE: Offene Laserchirurgie am Bewegungsapparat, Vol. 25 (1996), pp. 56-63.

Gehring W.J., Exploring the Homeobox (1993), pp. 215-221.

Kelly L.E., Purification and Properties of a 23kDa Ca2+-Binding Protein (1990), 271, pp. 661-666.

Sluyter, Radiofrequency Lesions in the Treatment of Cervical Pain Syndromes, Radionics, Inc. (1989).

Buchelt et al., LASERS IN SURGERY AND MEDICINE:Erb: YAG and Hol: YAG Laser Ablation of Meniscus and Intervertebral Discs, Vol. 12, No. 4 (1992), pp. 375-381.

Leu et al., DER ORTHOPADE: Endoskopie der Wirbelsaule:Minimal-invasive Therapie, Vol. 21 (1992), pp. 267-272.

Phillips et al., JMRI: MR Imaging of Ho:YAG Laser Diskectomy with Histologic Correlation, Vol. 3, No. 3, May/June 1993.

UNITED STATES PATENT AND TRADEMARK OFFICE
CERTIFICATE OF CORRECTION

PATENT NO. : 6,544,260 B1
DATED : April 8, 2003
INVENTOR(S) : Mark Markel, Hugh R. Sharkey and Gary S. Fanton It is certified that error appears in the above-identified patent and that said Letters Patent is hereby corrected as shown below:

Title page (cont'd),
Bromm et al., HUMAN NEUROBIOLOGY: Nerve Fibre Discharges, Cerebral Potentials and Sensations Induced by CO2 laser Stimulation, Vol. 3 (1984), pp. 33-40.

Kolarik et al., Photonucleolysis of Intervertebral Disc and it's Herniation, Vol. 51 (1990), pp. 69-71.

Vorwerck et al., Laserablation des Nucleus Pulposus: Optische Eigenschaften von Degeneriertem Bandscheibengewebe im Wellenlangenbereich von 200 bis 2200nm, Vol. 11, No. 6 (1989), pp. 725-728.

Wolgin et al., Excimer Ablation of Human Intervertebral Disc at 308 Nanometers, Vol. 9 (1989), pp. 124-131.

Davis, Early Experience with Laser Disc Decompression, Vol. 79 No. 1 (1992), j. Florida M.A.

Quigley et al., Laser Discectomy:Comparison of Systems, Vol. 19, No. 3 (1994), pp. 319-322.

Mehta et al., The Treatment of Chronic Back Pain: A Preliminary Survey of the Effect of Radiofrequency Denervation of the Posterior Vertebral Joints, Vol. 34 (1979), pp. 768-775.

Patil et al., Percutaneous Discectomy Using the Electomagnetic Field

Focusing Probe: A Feasability Study.

McCulloch et al., CMA JOURNAL: Percutaneous Radiofrequency Lumbar Rhizolysis (rhizotomy), Vol. 116, January 8, 1977.

Yonezawa et al., The System and Procedure of Percutaneous Intradiscal Laser Nucleotomy, Vol. 15, No. 11 (1990).

Sminia et al, Effects of 434 MHz Microwave Hyperthermia applied to the rat in the region of the cervical Spinal Cord, Vol. 3, No. 5 (1987), pp. 441-452.

Sluijter et al., Treatment of Chronic Back and Neck Pain by Percutaneous Therman Lesions, Vol. 3 (1981).

Auhll, Richard A., "The Use of the Resectoscope in Gynecology," Biomedical Business International, October 11, 1990, pp. 91-93.

UNITED STATES PATENT AND TRADEMARK OFFICE
CERTIFICATE OF CORRECTION

PATENT NO. : 6,544,260 B1
DATED : April 8, 2003
INVENTOR(S) : Mark Markel, Hugh R. Sharkey and Gary S. Fanton It is certified that error appears in the above-identified patent and that said Letters Patent is hereby corrected as shown below:

Title page (cont'd),
Christian, C. et al., "Allograft Anterior Cruciate Ligament Reconstruction with Patellar Tendon: An Endoscopic Technique", *Operative Techniques in Sports Medicine*, Vol. 1, No. 1, Jan. 1993, p. 50-57.

Houpt, J. et al., "Experimental Study of Temperature Distributions and Thermal Transport During Radiofrequency Current Therapy of the Intervertebral Disc", *SPINE*, Vol. 21, No. 15 (1996), pp. 1808-13.

Troussier, B. et al., "Percutaneous Intradiscal Radio-Frequency Thermocoagulation: A Cadaveric Study", *SPINE*, Vol. 20, No. 15 (Aug. 1995), pp. 1713-18.

Beadling, L., "Bi-Polar electrosurgical devices: Sculpting the future of arthroscopy", *Orthopedics Today*, Vol. 17, No. 1, January 1997, 4 pages.

Ellman International Mfg., Inc., 1989, Catalog, pp. 1-15, 20.

Cosset, J.M., "Resistive Radiofrequency (Low Frequency) Interstitial Heating (RF Technique), Interstitial Hyperthermia, 12/6/93, pp. 3-5, 37.

Attachment I: Competitive Literature on Generators with Bipolar Capabilities, IME Co., Ltd., pp. 60-86.

Attachment II: Competitive Literature on Bipolar Forceps and Footswitch Controls, IME Co., Ltd., pp. 87-104.

Column 1,
Line 9, after "6,068,628" insert -- , the --.
Line 39, after "indicate" delete "-".

Column 2,
Line 25, replace "surflces" with -- surfaces --.
Line 46, replace "arcticular" with -- articular --.

Column 3,
Line 11, replace "subehondral" with -- subchondral --.

Column 4,
Line 19, delete "fibrillated,".
Line 30, after "according" insert -- to --.

UNITED STATES PATENT AND TRADEMARK OFFICE
CERTIFICATE OF CORRECTION

PATENT NO. : 6,544,260 B1
DATED : April 8, 2003
INVENTOR(S) : Mark Markel, Hugh R. Sharkey and Gary S. Fanton It is certified that error appears in the above-identified patent and that said Letters Patent is hereby corrected as shown below:

Column 5,
Line 13, after "is" insert -- a --.

Column 6,
Line 27, replace "ilit" with -- unit --.
Line 52, "Second plurality" should not have been a new paragraph.

Column 8,
Line 17, replace "nonconducting" with -- non-conducting --.
Line 22, after "surface" insert -- , --.
Line 23, "First and second" should be a new paragraph.
Line 26, "First and second" should not be a new paragraph.
Line 40, after "determined" insert -- . --.
Line 59, replace "nonsymmetrical" with -- non-symmetrical --.

Column 10,
Line 42, after "1% of" insert -- , --.
Line 57, replace "40 W" with -- 40W --.

Column 11,
Lines 2, 12 and 27, replace "40 W" with -- 40W --.
Lines 37 and 50, replace "20 W" with -- 20W --.

Column 12,
Line 17, replace "oint" with -- joint --.
Line 46, after "can" insert -- be --.

Column 13,
Line 2, replace "the into" with -- into --.

Column 14,
Line 3, replace "before the" with -- before --.
Line 25, after "method" insert -- of --.
Line 30, replace "environmrent" with -- environment --.

Column 15,
Line 5, after "claim 15" insert -- , --.
Line 17, delete "Aid as".
Line 20, replace "18" with -- 25 --.
Line 27, after "claim 27" insert -- , --.
Line 28, replace "90" with -- 90° --.

UNITED STATES PATENT AND TRADEMARK OFFICE
CERTIFICATE OF CORRECTION

PATENT NO. : 6,544,260 B1
DATED : April 8, 2003
INVENTOR(S) : Mark Markel, Hugh R. Sharkey and Gary S. Fanton It is certified that error appears in the above-identified patent and that said Letters Patent is hereby corrected as shown below:

Column 15 (cont'd),
Line 30, replace "arthros" with -- arthroscopic --.
Line 40, replace "24" with -- 29 --.
Line 41, after "saline" insert -- , --.

Column 16,
Line 13, after "before" delete "the".
Line 19, after "method" insert -- of --.
Line 19, replace "35" with -- 33 --.

Signed and Sealed this

Thirteenth Day of December, 2005

JON W. DUDAS
*Director of the United States Patent and Trademark Office*